(12) United States Patent
Dugar

(10) Patent No.: US 12,226,379 B2
(45) Date of Patent: Feb. 18, 2025

(54) HIGHLY SUSTAINABLE COMPOSITIONS FOR MODULATION OF GENE EXPRESSION IN HUMAN SKIN, AND METHODS OF PRODUCTION THEREOF

(71) Applicant: Visolis Technologies, Inc., Dover, DE (US)

(72) Inventor: Deepak Dugar, Berkeley, CA (US)

(73) Assignee: VISOLIS, INC., Dover, DE (US)

( * ) Notice: Subject to any disclaimer, the term of this patent is extended or adjusted under 35 U.S.C. 154(b) by 0 days.

(21) Appl. No.: 18/107,060

(22) Filed: Feb. 8, 2023

(65) Prior Publication Data

US 2023/0248677 A1 Aug. 10, 2023

Related U.S. Application Data

(60) Provisional application No. 63/307,997, filed on Feb. 8, 2022.

(51) Int. Cl.
| | |
|---|---|
| *A61K 31/191* | (2006.01) |
| *A61K 8/365* | (2006.01) |
| *A61K 9/00* | (2006.01) |
| *A61K 9/06* | (2006.01) |
| *A61Q 19/00* | (2006.01) |
| *C12P 7/56* | (2006.01) |

(52) U.S. Cl.
CPC ............ *A61K 31/191* (2013.01); *A61K 8/365* (2013.01); *A61K 9/0014* (2013.01); *A61K 9/06* (2013.01); *A61Q 19/00* (2013.01); *C12P 7/56* (2013.01)

(58) Field of Classification Search
None
See application file for complete search history.

(56) References Cited

U.S. PATENT DOCUMENTS

2022/0331219 A1 * 10/2022 Anglenius ............ A61Q 19/007

* cited by examiner

*Primary Examiner* — Nannette Holloman
(74) *Attorney, Agent, or Firm* — Rivka Friedman

(57) ABSTRACT

Formulations containing biologically-produced, high-purity R-mevalonolactone are provided for modulating the expression of genes and metabolism related to epidermal turnover, hyaluronic acid synthesis, barrier function, anti-aging elasticity, extracellular matrix degradation, inflammation, stress, and pigmentation in human skin. The biologically-produced, high-purity R-mevalonolactone may be used as an ingredient in pharmaceutical, food, or cosmetic products and may be applied topically or ingested for modulation of gene expression and metabolism.

43 Claims, 8 Drawing Sheets

HIGHLY SUSTAINABLE COMPOSITIONS FOR MODULATION OF GENE EXPRESSION IN HUMAN SKIN, AND METHODS OF PRODUCTION THEREOF

BACKGROUND

1. Field of the Invention

The present invention generally relates to formulations containing mevalonic acid derivatives. More particularly, the present invention generally relates to healthcare formulations containing high-purity, low odor, low color mevalonolactone, which can modulate expression of various epithelial tissue-related genes.

2. Description of the Related Art

From the moment of birth, human epithelial cells, like those in skin, undergo aging as the result of intrinsic biological senescence and external factors, such as exposure to toxins and ultraviolet radiation. This process is accelerated after adolescence, with visible effects often appearing just after 20 years of age and progressing until death. Visible effects of skin aging can include, for example, development of fine wrinkles, dryness, loss of elasticity (sagging), and discolored or "mottled" appearance.

At the molecular level, these effects of skin aging are characterized by the progressive breakdown of the epidermal extracellular matrix ("ECM"). The ECM is the largest component of human skin and is primarily comprised of fibrous structural proteins, such as collagen and elastin which provide strength and resilience to the network. The second major class of molecules in the ECM is the glycosaminoglycans ("GAGs") (also called proteoglycans), such as hyaluronic acid, which maintains hydration in connective tissue and promotes the proliferation of new epithelial cells among other vital cellular functions.

Exposure to external factors leading to skin aging (extrinsic aging) can at least be partially mitigated by lifestyle choices. Such choices include limiting skin exposure to the sun or using sun protection, making informed dietary choices, and abstinence from smoking.

To maintain strong, healthy-looking skin, ECM components, such as those listed above, must be continuously produced by epithelial cells to offset natural tissue breakdown and any damage done by oxygen radicals or ultraviolet radiation. However, as humans age past adolescence, production of ECM components naturally declines, with decreases in collagen, elastin, and hyaluronic acid production beginning at age 20. Due to the widespread desire among individuals for healthy, youthful skin, numerous products have been developed aimed at increasing levels of these ECM components, typically by oral or topical supplementation.

Despite the large market for such products, the efficacy of oral collagen supplements has been called into question by many scientists due to a lack of comprehensive studies and the basic anatomical fact that orally-consumed proteins are broken down in the stomach, meaning oral collagen is not delivered to the skin as a polymer. Furthermore, as collagen is a major connective tissue component found throughout the body, such supplements cannot be "targeted" to the skin, or facial skin in particular.

Topical compositions containing hyaluronic acid ("HA") and other large molecular weight ECM components suffer from a similar failure of the supplement failing to reach the intended tissue. HA has a molecular weight in the range of 5 million daltons, and the average HA molecule has a diameter of 3,000 nm. Contrasted with the average intercellular space in the epithelium of 15 to 50 nm, such compositions can face great challenges to penetrate beyond the surface of the skin to which they are applied. Other active ingredients, like retinol derivatives, are known to stimulate cell turnover, but can be complicated to formulate and deliver. They may also cause side effects like increased skin sensitivity and dryness.

In light of these issues, it is apparent that promoting synthesis of these large molecular weight ECM components, along with cellular growth in the target tissue, is preferable to external supplementation. The genes associated with synthesis of collagen, elastin, and hyaluronic acid in humans are well characterized and show an age-related decline in expression coinciding with the decline of the extracellular matrix and visual progression of skin aging. Genes associated with stimulation of cell growth and differentiation are also well characterized and show an age-related decline in expression coinciding with the visual progression of skin aging.

Furthermore, there is a rising need for more sustainable solutions that address the challenges highlighted previously. Traditional processes for production of ingredients, like retinol, rely on fossil fuel raw materials, such as coal and petroleum. They also require multiple steps of synthesis and generate significant amount of waste and carbon emissions per unit of product. It is estimated that one kg of retinol production might result in an equivalent of 40 kg of $CO_2$ greenhouse gas emissions. Moreover, even when renewable raw materials are used, the resulting products are generally plagued by poor process efficiencies, high amounts of undesirable side products, and the use of organic solvents and/or petrochemicals in processing, which negatively impact the sustainability benefit of using renewable starting materials. Therefore, there continues to be a need for newer ingredients and processes that are more sustainable in the production of sustainable healthcare formulations.

JPH09221406A discloses a cosmetic skin treatment composition that includes 0.001-10 wt % mevalonolactone blended with amino acids to provide beautiful skin effect.

DE19918761 discloses cosmetic preparations that include mevalonolactone for reinforcing the barrier function of the skin.

DE10148266 discloses cosmetic compositions that include mevalonolactone for treatment of UV skin damage.

JP4854110 discloses use of mevalonolactone as an active ingredient for anti-inflammatory anti-allergic effects via histamine release inhibition.

It has now been found that healthcare formulations containing high purity mevalonolactone, can modulate expression of various epithelial tissue-related genes. The invention in the present application is by way of a finding that mevalonolactone effects gene expression regulation which, to the knowledge of the present inventors, has not been known heretofore. Another aspect of the present invention is a high-purity, low odor, low color mevalonolactone, which has not been known heretofore. Characteristics like low odor are important for using mevalonolactone in a healthcare application like a sustainable, fragrance free, topical compositions to be used on the face.

SUMMARY

One or more embodiments generally concern a gene modulation formulation for modulating expression of one or more genes. Generally, the formulation comprises mevalonolactone, wherein the mevalonolactone exhibits an APHA color of less than 500 units of parts per million of platinum-cobalt to water as measured by ASTM D1209. Furthermore, the mevalonolactone comprises less than 5 weight percent of fermentation byproducts, mal-odor causing bodies, ethyl acetate, dichloromethane, tetrahydrofuran, isopropanol, petrochemicals, or combinations thereof, based on the total weight of the mevalonolactone.

One or more embodiments generally concern a method of forming a dermatological formulation. Generally, the method comprises: (a) providing an aqueous solution of mevalonolactone, wherein the aqueous solution exhibits an APHA color of less than 500 units of parts per million of platinum-cobalt to water as measured by ASTM D1209 and comprises less than 5 weight percent of fermentation byproducts, ethyl acetate, dichloromethane, tetrahydrofuran, isopropanol, petrochemicals, or combinations thereof, based on the total weight of the solution; and (b) combining the aqueous solution with at least one additive to thereby form the dermatological formulation.

One or more embodiments generally concern a purified mevalonolactone solution comprising: (a) mevalonolactone, wherein at least 95 weight percent of the mevalonolactone comprises at least 95 weight percent of R-mevalonolactone based on the total weight of the mevalonolactone; and (b) water. Furthermore, the solution exhibits an APHA color of less than 500 units of parts per million of platinum-cobalt to water as measured by ASTM D1209 and comprises less than 5 weight percent of fermentation byproducts, ethyl acetate, dichloromethane, tetrahydrofuran, isopropanol, petrochemicals, or combinations thereof, based on the total weight of the solution.

BRIEF DESCRIPTION OF THE FIGURES

Embodiments of the present invention are described herein with reference to the following drawing figures, wherein.

DETAILED DESCRIPTION

Figure 1:
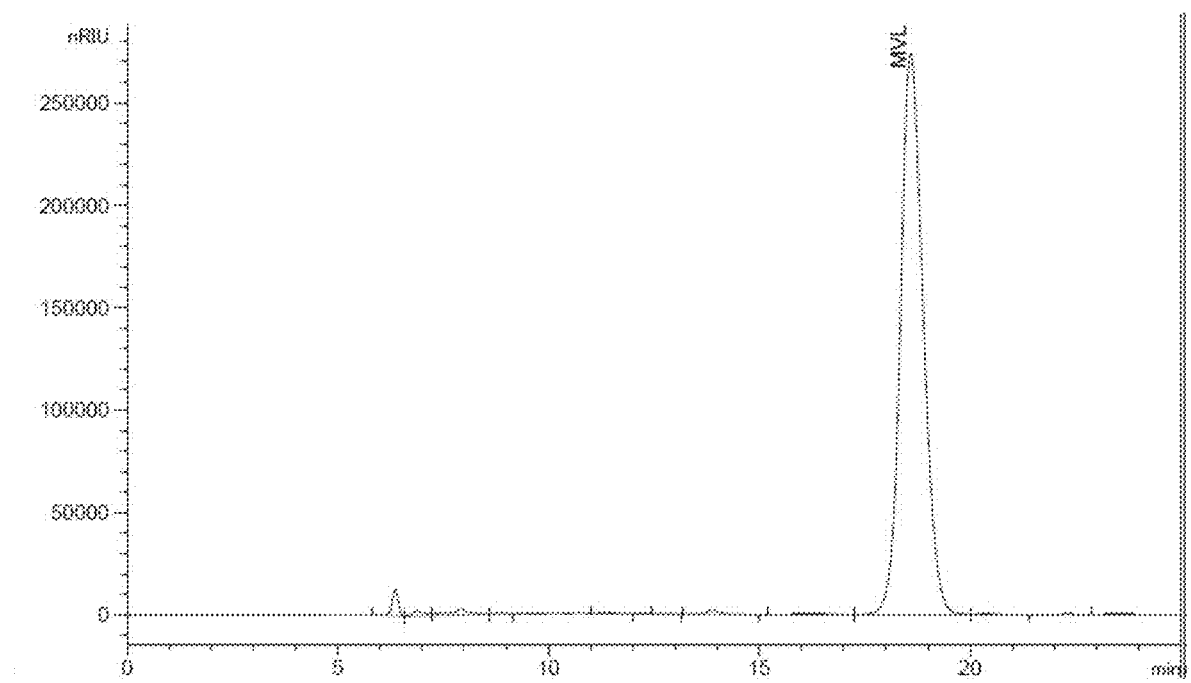
FIG. 1 depicts a HPLC chromatogram from the end of the fermentation process described herein.

The present disclosure generally relates to the production of sustainable formulations containing biologically-produced, high-purity mevalonolactone ("MVL"), particularly R-mevalonolactone ("R-MVL"), for modulating expression of genes and metabolism related to epidermal turnover, hyaluronic acid synthesis, barrier function, anti-aging elasticity, extracellular matrix degradation, inflammation, stress, energy metabolism, and/or pigmentation in human epithelial cells. As discussed below, this biologically-produced high-purity R-MVL may be used as an ingredient in pharmaceutical, food, and/or cosmetic products and may be applied topically or ingested for modulation of gene expression and metabolism.

It should be noted that R-mevalonolactone may exist in equilibrium with its ring-open form, R-mevalonic acid, and the corresponding anion form, R-mevalonate, depending on pH and water concentration. As used herein, these terms may be used interchangeably and collectively as R-mevalonolactone or R-MVL. Likewise, the term "mevalonolactone" or MVL may also be used interchangeably with its ring-open form, mevalonic acid, and its corresponding anion form, mevalonate.

As discussed below in greater detail, a process has been developed for the biological production of highly sustainable, high-purity R-mevalonolactone from bio-based feedstocks (i.e., the MVL product). It has been discovered that this R-MVL product can be used to produce and provide topical (i.e., external skin) compositions that can increase expression of various genes or gene families by at least 1, 5, 10, 20, 30, 40, 50, 75, or 100 percent, which can enhance the local synthesis of vital ECM components, such as collagen, elastin, and hyaluronic acid.

The Gene Modulation Formulations

It has been discovered that sustainable formulations containing the MVL product, such as formulations containing 0.05 to 10 weight percent of the MVL product, exhibited potent broad-spectrum modulation of gene expression in human epithelial skin cells. Specifically, in certain embodiments, it was found that compositions containing 0.1 to 1.0 weight percent of the MVL product modulated gene expression in human epithelial cells by increasing expression of genes related to epithelial turnover, hyaluronic acid synthesis, barrier function, and anti-aging elasticity by at least 10 percent and by decreasing expression of genes related to ECM degradation, inflammation, and pigmentation by at least 10 percent. These gene modulation formulations and the MVL products used to produce these formulations are described in greater detail below.

It should be noted that any of the following properties and ranges associated with: (i) the process for producing the MVL product, (ii) the process for producing the gene modulation formulations containing the MVL product, (iii) the MVL product itself, and (iv) the formulations themselves are not mutually exclusive, even if they are listed separately, and may be combined in any combination, as long as such combination does not create a conflict between any of the properties or ranges.

In one or more embodiments, the MVL product can be a solvent-free, optically pure, and high-purity MVL. As discussed below in greater details, these features and characteristics are largely derived from the processes and materials used to produce the MVL.

In one or more embodiments, the gene modulation formulations of the present disclosure may comprise at least 0.01, 0.1, or 0.05 weight percent the MVL product, such as the solvent-free, optically-pure, high-purity MVL, based on the total weight of the formulation. Generally, in one or more embodiments, the gene modulation formulations may comprise at least 0.01, 0.05, 0.01, 0.2, 0.3, 0.4, 0.5, 0.6, 0.7, 0.8, 0.9, or 1 weight percent and/or less than 40, 30, 20, 15, 10, 9, 8, 7, 6, 5, 4, 3, 2, or 1 weight percent of MVL, such as mevalonolactone, mevalonic acid, and/or a salt of mevalonic acid, based on the total weight of the formulation. It should be noted that these weight percentages of mevalonolactone, mevalonic acid, and/or a salt of mevalonic acid may pertain to the colorless MVL aqueous solutions discussed below and produced in accordance with the purification techniques described herein. Furthermore, these weight percentages of mevalonolactone, mevalonic acid, and/or a salt of mevalonic acid may also apply to the solvent-free, optically pure, and high-purity MVL.

In one or more embodiments, the MVL product in the gene modulations of the present disclosure may be predominantly R-MVL, which is the biologically active isomer of MVL (relative to the S-version). In various embodiments, the MVL product in the gene modulation formulations comprise at least 95, 99, 99.9, 99.99, or 99.999 weight percent of R-MVL, based on the total weight of the MVL product.

Additionally, in various embodiments, the gene modulation formulations of the present disclosure can be substantially free of undesirable byproducts. In various embodiments, the gene modulation formulations produced herein may comprise less than 5, 4, 3, 2, 1, 0.5, 0.1, 0.05, 0.01, 0.005, 0.001, 0.0005, 0.0001, 0.00005 or 0.00001 weight percent of one or more undesirable byproducts, based on the total weight of the formulation. Exemplary undesirable byproducts may include, but are not limited to, fermentation byproducts (e.g., acetic acid, citric acid, glucose, pyruvic acid, ethanol, pyruvate, glycerol, and/or lactic acid), organic solvents (e.g., ethyl acetate, methyl ethyl ketone, dibasic esters, dichloromethane, tetrahydrofuran, and/or isopropanol), petrochemicals, color bodies, odorous bodies, inorganic salts, and/or organic salts. It should be noted that the above weight ranges regarding the above undesirable byproducts may be applicable to any individual byproduct listed above or any combination thereof. As used herein, a "petrochemical" refers to a substance obtained by the refining and processing of petroleum or natural gas.

Additionally or alternatively, in various embodiments, the gene modulation formulations of the present disclosure can be substantially free of ceramide, glucosylceramide, garactosylceramide, and/or sphyigomyelin. In various embodiments, the gene modulation formulations produced herein may comprise less than 5, 4, 3, 2, 1, 0.5, 0.1, 0.05, 0.01, 0.005, 0.001, 0.0005, 0.0001, 0.00005 or 0.00001 weight percent of ceramide, glucosylceramide, garactosylceramide, and/or sphyigomyelin, based on the total weight of the formulations. It should be noted that the above weight ranges regarding the above products may be applicable to any individual product listed above or any combination thereof.

The gene modulation formulations for topical use containing the highly-sustainable, high-purity MVL of the present disclosure may be developed in various forms including, but not limited to, a mist, a lotion, an emulsion, a milk, a pack, a gel, a cream, an ointment, a granule, a powder, a foam, or the like. In one or more embodiments, such formulations of the present disclosure may contain at least one, two, three, or four of the following additives without departing from the scope of attaining the object of the present disclosure: carotenoid-type coloring elements, such as lutein, astaxanthin and fucoxanthin; vegetable oils, such as olive squalane, rice squalane, rice germ glycerides, jojoba oil, castor oil, safflower oil, olive oil, macadamia nut oil, and sunflower oil; waxes, such as beeswax, fruit wax, and carnauba wax; ester oils, such as octyldodecyl myristate, cetyl palmitate, isostearyl isostearate, and isopropyl myristate; lower alcohols, such as ethanol; higher alcohols, such as cetanol, behenyl alcohol, stearyl alcohol, and a branched long chain aliphatic alcohol; sterols and their derivatives, such as cholesterol, phytosterol, branched fatty acid cholesterol ester, macadamia nut fatty acid phytosteryl ester; processed oils, such as hydrogenated oil; higher fatty acids, such as stearic acid, myristic acid, isostearic acid, oleic acid, iso-type long chain fatty acid, and anteiso long chain fatty acid; terpenes, such as bakuchiol, limonene and hydrogenated bisabolol; triglycerides, such as glyceryl tricaprylcaprate, glyceryl 2-ethylhexanoate, glyceryl triisotype long chain fatty acid ester, and glyceryl tripalmitate; anionic surfactants, such as sodium cetylsulfate and N-stearoyl-L-glutamic acid salt; nonionic surfactants, such as polyoxyethylene alkyl ether, polyoxyethylene fatty acid ester, polyoxyethylene polyhydric alcohol fatty acid ester, polyoxyethylene hydrogenated castor oil, polyhydric alcohol fatty acid ester; modified silicone, such as polyoxyethylene-modified silicone, polyglycerin fatty acid ester, and sucrose ester; cationic surfactants, such as tetraalkylammonium salt; amphoteric surfactants, such as betaine type, sulfobetaine type, and sulfoamino-acid surfactants; natural type surfactants, such as lecithin, lysophosphatidylcholine, ceramide, and cerebroside; pigments, such as titanium oxide and zinc oxide; coloring pigments, such as iron oxide; tar type color additives; silicone oils, such as dimethylpolysiloxane, methylphenylpolysiloxane, and cyclic silicone; preservatives, such as parabens and phenoxyethanol; hydrocarbons, such as paraffin and vaseline; antioxidants, such as dibutylhydroxytoluene; inorganic salts, such as sodium chloride, magnesium chloride, sodium sulfate, potassium nitrate, sodium sulfate, sodium metasilicate, and calcium chloride; organic acids and their salts, such as sodium citrate, potassium acetate, sodium succinate, sodium asparaginate, sodium lactate, dichloroacetic acid, and glycyrrhizinic acid; organic amines and their salts, such as ethanol amine hydrochloride, ammonium nitrate, arginine hydrochloride, diisopropylamine salt, urea, and decarboxycarnosine; chelating agents, such as edetic acid; thickeners, such as xanthane gum, carboxyvinyl polymer, carrageenan, pectin, alkyl-modified carboxyvinyl polymer, and agar; neutralizing agents, such as potassium hydroxide, diisopropanolamine, and triethanolamine; ultraviolet absorbents, such as hydroxymethoxybenzophenonesulfonate salt; polyhydric alcohols, such as dipropylene glycol, marvitol, 1,3-butylene glycol, glycerin, propylene glycol, sorbitol, diglycerin, and raffinose; vitamins, such as various amino acids, ascorbic acid, biotin, and tocopherol; and vitamin derivatives, such as ascorbic acid sulfate ester salt, ascorbic acid phosphate ester salt, and tocopherol nicotinate; and combinations thereof. In various embodiments, the gene modulation formulations produced herein may comprise at least 0.1, 0.5, 1, 2, 3, 4, or 5 and/or less than 99, 95, 90, 80, 70, 60, 50, 40, 30, 20, 15, or 10 weight percent of one or more additives, based on the total weight of the formulation.

Additionally or alternatively, in various embodiments, the gene modulation formulations of the present disclosure can comprise bakuchiol and/or lactic acid. In such embodiments, the gene modulation formulations produced herein may comprise at least 0.1, 0.5, 1, 1.25, 1.5, 1.75, 2, 2.25, 2.5, 2.75, 3, or 3.25 and/or less than 40, 30, 20, 15, 10, or 5 weight percent of bakuchiol and/or lactic acid, based on the total weight of the formulation. It has been observed that bakuchiol, lactic acid, and MVL can have a synergistic effect on expression of certain genes related to skincare.

Additionally or alternatively, in various embodiments, the gene modulation formulations of the present disclosure can comprise bakuchiol, lactic acid, ceramide, hyaluronic acid, retinal, retinol, Vitamin C, a peptide, or a combination thereof. In such embodiments, the gene modulation formulations produced herein may comprise at least 0.1, 0.5, 1, 1.25, 1.5, 1.75, 2, 2.25, 2.5, 2.75, 3, or 3.25 and/or less than 40, 30, 20, 15, 10, or 5 weight percent of bakuchiol, lactic acid, ceramide, hyaluronic acid, retinal, retinol, Vitamin C, a peptide, or a combination thereof, based on the total weight of the formulation.

In one or more embodiments, the gene modulation formulations described herein can comprise a pH of at least 1.5, 2.0, or 2.5 and/or not more than 7.5, 7.0, 6.5. 6.0, 5.5, 5.0, or 4.9.

In one or more embodiments, the gene modulation formulations described herein may comprise a viscosity of at least 500, 1,000, 1,500, 2,000, 2,500, 3,000, 3,500, or 4,000 centipoise at 25° C.

As discussed above, the gene modulation formulations described herein can simultaneously modulate expression of at least two or more genes involved in collagen synthesis, elasticin synthesis, hyaluronic acid synthesis, skin barrier function, cell turn over regulation, skin pigmentation, skin inflammation, and/or cortisol production.

In one or more embodiments, the gene modulation formulations produced herein can be used as topical (i.e., external skin) compositions that can increase or decrease expression of various genes or gene families by at least 1, 5, 10, 20, 30, 40, 50, 75, or 100 percent to thereby enhance local synthesis of vital ECM components, such as collagen, elastin, and hyaluronic acid, and/or modulate metabolism involved in stress response by reducing production of cortisol in human epithelial skin cells. These genes can include, for example, COL1A1, COL1A2, COL4A1, ELN, EMILIN1, EMILIN2, MFAP5, FN1, LAMA1, TIMP1, TIMP2, TIMP3, TIMP4, HAS1, HAS2, HAS3, HABP4, HAPLN1, EGF, FGF7, HBEGF, KRT1, KRT2, KRT4, DEFA1, MMP1, MMP2, MMP3, MMP7, MMP9, NFATC1, IL1A, IL1B, TNFA, SELE, SELL, EDN1, EDN2, EDN3, PTGS2 (COX2), POMC, or combinations thereof.

In one or more embodiments, the gene modulation formulations produced herein can be used as topical (i.e., external skin) compositions that can increase expression by at least 1, 5, 10, 20, 30, 40, 50, 75, or 100 percent as measured 24 hours after application of at least 1, 2, 3, 4, 5, 6, 7, or 8 of the following genes: COL1A1, COL1A2, COL4A1, ELN, EMILIN1, EMILIN2, MFAP5, FN1, LAMA1, TIMP1, TIMP2, TIMP3, TIMP4, HAS1, HAS2, HAS3, HABP4, HAPLN1, EGF, FGF7, HBEGF, KRT1, KRT2, KRT4, and DEFA1. For example, an increase in gene expression of at least 10 percent refers to a positive change in expression of magnitude 0.1 or greater relative to a negative control.

In one or more embodiments, the gene modulation formulations produced herein can be used as topical (i.e., external skin) compositions that can decrease expression by at least 1, 5, 10, 20, 30, 40, 50, 75, or 100 percent as measured 24 hours after application of at least 1, 2, 3, 4, 5, 6, 7, or 8 of the following genes: MMP1, MMP2, MMP3, MMP7, MMP9, NFATC1, IL1A, IL1B, TNFA, SELE, SELL, EDN1, EDN2, EDN3, PTGS2 (COX2), and POMC. For example, a decrease in gene expression of at least 10 percent refers to a negative change in expression of magnitude 0.1 or greater relative to a negative control.

In one or more embodiments, the gene modulation formulations produced herein can be used as topical (i.e., external skin) compositions that can decrease production of cortisol in human epithelial skin cells by at least 1, 5, 10, 20, 30, 40, 50, 75, or 100 percent as measured 24 hours after application.

In one or more embodiments, the gene modulation formulations produced herein can be used as topical (i.e., external skin) compositions that can increase the skin hydration level, decrease the skin roughness level, and/or decrease the skin spots level in a human target by at least 1, 5, 10, 20, 30, 40, 50, 75, or 100 percent over a four-week period with daily application (one or twice a day), relative to a base line using no treatment.

In one or more embodiments, the gene modulation formulations produced herein can be used as a sanitizer for sanitizing a surface that can kill at least 99.9 percent of model bacteria present on the treated surface.

The MVL Production Processes

MVL has traditionally been prepared by either chemical catalysis or fermentation followed by solvent processing. Generally, the catalytic process leads to a mix of R and S configurations of mevalonolactone, which is not ideal for use in the formulations of the present disclosure since only the R-version is biologically active. Furthermore, both conventional processes utilize petrochemical inputs and, therefore, are not environmentally sustainable.

Moreover, conventional fermentation techniques utilize complex medium for propagation of the microbes, which may result in added residual impurities at the end of fermentation, thereby necessitating use of techniques like solvent processing, which are not as sustainable. For instance, the process originally disclosed by Tokyo Noko University and subsequently utilized by Adeka for their production of MVL utilizes a microbe *Saccharomycopsis fibuligera* for fermentation. For MVL production, *S. fibuligera* is generally propagated in a complex medium containing peptone, malt extract, yeast extract, or combinations thereof. At the end of such fermentation, a lot of impurities from these complex organic reagents are left in the broth. Furthermore, the MVL concentration is quite low at less than 10 g/l even after 12 days of fermentation. One of the ways to purify this low concentration MVL from the Adeka process is via acidification of the broth, followed by solvent extraction using petrochemicals like ethyl acetate or methyl ethyl ketone, which are volatile organic compounds (VOCs) of fossil origin. The solvent layer enriched in MVL is then separated and the solvent is evaporated to leave behind the very high boiling (>260° C.) MVL, along with other impurities including residual solvent. Such processes and end compositions are not as sustainable and environmentally friendly.

In contrast to the conventional methods discussed above, the highly-sustainable, high-purity, solvent-free MVL product used in the formulations described herein is generated through a novel fermentation of renewable feedstocks by a microorganism in a defined minimal media, followed by a downstream processing method that does not include a solvent extraction step that generally involves use of petrochemicals. As discussed below in greater detail, the purified mevalonolactone, mevalonic acid, and/or a salt of mevalonic acid may be produced by: (a) fermenting an initial feedstock to form an unpurified solution comprising mevalonolactone, mevalonic acid, and/or a salt of mevalonic acid; (b) optionally, contacting the unpurified solution with an acid to thereby form an acidic mixture; and (c) purifying the mixture with a wiped film evaporator, a falling film evaporator, rotary evaporator, an electrodialysis device, and/or an electro-deionization device to thereby form a purified solution comprising mevalonolactone, mevalonic acid, and/or a salt of mevalonic acid.

In one or more embodiments, the fermentation feedstock providing carbon source includes, but is not limited to, at least one or more of a starch-based glucose; a cellulosic hydrolysates containing one or more sugars including glucose, xylose, arabinose, mannose, and rhamnose; glycerol; anaerobic digests of food and/or agricultural waste containing one or more short chain acids including acetic acid, lactic acid, propionic acid, butyric acid and isovaleric acid; ethanol; and/or disaccharides, such as sucrose. Other sustainable inputs may include carbon dioxide and/or carbon monoxide.

The microorganism for fermentation may include, but is not limited to, a K-12 *E. coli* strain expressing genes necessary for synthesis of MVL or a yeast like *S. cerevisiae* or *I. orientalis*. The microorganism may also exhibit the property of minimal flux to side products like acetic acid, pyruvic acid, ethanol, glycerol, lactic acid, etc., by virtue of reduced activity or elimination of activity in the corresponding pathway via gene, transcript, and/or protein level changes.

In one or more embodiments, the fermentation process is conducted in a batch or fed-batch mode with a defined growth medium containing inorganic salts with one or more of the above listed renewable carbon sources, preferably glucose. In various embodiments, the defined growth medium can comprise glucose, ammonium sulfate, citric acid, potassium phosphate monobase, magnesium sulfate anhydrous, calcium sulfate dihydrate, ferrous sulfate heptahydrate, thiamine hydrochloride, and a trace metal solution. For example, 1 L of the batch medium may be formulated with: glucose 20 g, ammonium sulfate 7.5 g, triammonium citrate 9.2 g, potassium phosphate monobasic 1.361 g, magnesium sulfate anhydrous 0.602 g, calcium sulfate dihydrate 21.52 mg, ferrous sulfate heptahydrate 0.267 g, thiamine hydrochloride 20 mg, and trace metal solution 8 mL. In certain embodiments, the 1 L of trace metal solution can be formulated with: concentrated sulfuric acid 10 mL, $CoSO_4 \cdot 7H_2O$ 0.6 g, $ZnSO_4 \cdot 7H_2O$ 0.6 g, $Na_2MoO_4 \cdot 7H_2O$ 0.2 g, $H_3BO_3$ 0.1 g, $MnSO_4 \cdot H_2O$ 0.3 g, and $CuSO_4 \cdot 5H_2O$ 5 g. The benefit of such a batch medium is minimal residual organic, undefined impurities, and/or trace ionic impurities that can easily be separated from MVL at the end of fermentation.

Temperature during fermentation may be at least 20° C., 30° C., or 35° C. and/or less than 50° C., 45° C., or 40° C. In certain embodiments, the temperature during fermentation is between 20 to 50° C., most preferably at around 37° C. Oxygen content of the media may be maintained at a rate of at least 1, 5, 10, or 15 and/or less than 50, 40, 30, or 20 percent saturation in the media. In certain embodiments, the oxygen content of the media may be maintained at a rate between 1 to 50 percent of saturation in the media, most preferably at 20 percent of saturation in the media.

Glucose may continuously fed to the fermentation vessel to maintain a concentration of below 1 g/L once the initially batched glucose is exhausted. The pH during fermentation may be maintained at a pH of at least 3, 4, 5, 6, or 6.5 and/or less than 7.5, 7, or 6.9. In certain embodiments, the pH is maintained at 3 to 7.5, most preferably at 6.8. The pH may be maintained via the addition of a suitable base such as, but not limited to, ammonium hydroxide, calcium carbonate, sodium hydroxide, or calcium hydroxide, to neutralize the acidic fermentation products, including MVL.

Fermentation may be conducted over a period of 60 to 150 hours, resulting in an MVL concentration of at least 20, 50, 70, or 100 g/L of the final fermentation volume. In certain embodiments, the final MVL concentration is at least 50 g/l, preferably at least 100 g/L.

FIG. 1 provides a representative high pressure liquid chromatography (HPLC) chromatogram from the end of a typical fermentation of the present disclosure utilizing a *E. coli*-based engineered microbe reaching a concentration of 79 g/l MVL. As evident from the chromatogram in FIG. 1, there are no detectable peaks at the retention times corresponding to metabolites like acetate, pyruvate, glycerol, ethanol, etc. Other molecules, like citric acid and glucose, added to the fermentation media are also completely exhausted by end of fermentation as there is no detectable peak at the corresponding retention times. As discussed below, this chromatogram can be used to measure the purity of the MVL by analyzing and measuring the peaks present in the chromatogram. The presence of an almost solitary peak, such as depicted in FIG. 1, is indicative of a high-purity MVL.

Downstream processing used to obtain the solvent-free, optically-pure R-MVL begins at the end of fermentation with a "broth" containing the microbial cells, water, residual salts, and at least 0.05, 0.1, 0.5, 1, or 2 and/or less than 25, 20, or 15 weight percent of MVL, based on the total weight of the broth. Under these conditions, in one or more embodiments, the primary form of MVL is in its mevalonate anion form along with a corresponding cation, such as calcium $(Ca(MVL)_2)$, which is two deprotonated mevalonic acid molecules in solution with one calcium as the counter-ion.

At the end of fermentation, the resulting broth may contain minute amounts of aggregate side products (e.g., acetic acid, pyruvic acid, ethanol, glycerol, lactic acid, etc.) relative to the MVL concentration in the broth. In one or more embodiments, the broth after fermentation may comprise an aggregate side product concentration that is less than 0.2, 0.1, 0.02, or 0.01 times the MVL concentration in the broth.

This resulting broth may be further purified and concentrated by contacting the broth with one or more absorbents and/or concentrated acid (e.g., sulfuric acid). Exemplary absorbents can include, for example, cation exchange resins, anion exchange resins, activated carbon, charcoal, or a combination thereof. In various embodiments, the resulting broth after fermentation may be concentrated by evaporation, reverse osmosis, forward osmosis, electrodialysis, or a combination thereof.

In one or more embodiments, the resulting broth may be first acidified by the addition of sulfuric acid until the pH reaches 3.0, well below the pKa of MVL, which is approximately 4.2. Thus, the primary form of MVL under this condition is the protonated form that exists in equilibrium with the lactone form, and sulfate becomes the counter ion for calcium. The highly insoluble $CaSO_4$ then precipitates from solution. $CaSO_4$ is a well-known flocculent of microbial cells. Interactions between $CaSO_4$ and the bacterial membranes result in the clumping of cells and cell debris, and the formation of a "cake," as these clumps aggregate with the $CaSO_4$ salt. This results in the majority of cells and other solids forming cake, and more than 90 percent of the produced MVL remaining in the aqueous layer on top (also referred to as the supernatant). The cake can be removed by filtration and/or centrifugation. The remaining solids may be removed by filtration, for example, by a cross flow or tangential flow filtration unit using a membrane with a molecular weight cutoff of 1 to 100 kDa.

Subsequently, the remaining MVL-containing solution can then be further concentrated to a desired level by evaporation or filtration techniques, such as in a rotary evaporator, falling film evaporator, and/or wiped film evaporator. For example, the remaining solution may be processed in a standard lab rotary evaporator and/or a falling film evaporator at a temperature in the range of 40° C. to 70° C. and a pressure of 40 to 200 millibar in order to remove at least 99% of the remaining water in the solution. Optionally, after evaporation and/or filtration, the remaining crude MVL solution can be subjected to further treatment in a wiped film evaporator at less severe conditions, such as at a temperature in the range of 50 to 120° C. and a pressure of 0.1 to 10 mmHg, more preferably at a temperature of about 70° C. and a pressure of 0.3 mmHg. This optional and additional treatment may get rid of compositions that have higher boiling points than water, but lower boiling points than MVL.

Afterwards, the remaining crude MVL solution may be subsequently distilled in a wiped film evaporator at low temperatures, such as in the range of 90 to 200° C., 100 to 150° C., 110 to 130° C., or about 120° C., and high vacuum pressures, such as in the range of 0.1 to 10 mmHg, 0.2 to 5 mmHg, or about 0.3 mmHg. Furthermore, the residence time within the wiped film evaporator may be in the range of 20 to 1,000 seconds, 20 to 500 seconds, 20 to 200 seconds, 20 to 100 seconds, or preferably about 30 seconds. Consequently, the wiped film evaporator and the above conditions may provide a high-purity MVL.

In contrast to prior art techniques, the use of a wiped film evaporator for distillation allows for the formation of a high-purity MVL with less undesirable byproducts. Furthermore, the inventive purification techniques described herein minimize dehydration of MVL to side products, such as anhydromevalonolactone, during distillation.

This high-purity MVL formed from the aforementioned purification techniques can be diluted back with water to obtain a colorless aqueous solution of MVL at a desired concentration for various uses. For instance, water may be added to the high-purity MVL to obtain a 10% solution. If the purity is not as desired, the above optional step involving the wiped film evaporator may be utilized. Consequently, this can create an optional purification loop using the wiped film evaporator as discussed herein. In such embodiments, this optional purification loop may comprise at least 1, 2, 3, or 4 passes through the wiped film evaporator under the conditions described herein.

Another possible purification method for producing high-purity MVL involves exploiting the charged nature of MVL via the use of ion-selective membranes to selectively recover high-purity MVL. Such recovery can be done with an electrodialysis device and/or an electro-deionization device. For example, fermentation may be performed as described above by utilizing sodium hydroxide as a base to maintain pH between 6.1 to 6.9. At the end of fermentation, various solids, such as cells and cellular debris, may be removed using a centrifuge and/or filtration. Exemplary filtration could involve a cross flow and/or tangential flow filtration unit using a membrane with a molecular weight cutoff of 1 to 100 kDa. Subsequently, the clarified broth may then be passed through an electrodialysis device and/or an electro-deionization device to remove any inorganic salts, so as to obtain a sodium sulfate-rich concentrate stream. This low inorganic salts MVL solution may then be passed again through a second and/or an electro-deionization device so as to obtain a high-purity mevalonate salt in the concentrate stream. Alternatively, the clarified broth may only pass through an electrodialysis device and/or an electro-deionization device once to obtain a mevalonate salt solution in the concentrate stream, which is substantially decolorized and substantially de-odorized.

The treatment in the electrodialysis device and/or the electro-deionization device can occur for at least 1, 10, 20, 30, 40, 50, 60, 70, 80, 90, 100, 150, 200, 250, 300, 350, or 400 minutes and/or less than 500 minutes. Furthermore, in certain embodiments, the electrodialysis device and/or the electro-deionization device can operate at a voltage of 1 to 10 volts, preferably at about 5 volts.

It should be noted that, in certain embodiments, the methods for producing the MVL solutions and formulations do not involve columns packed with ion exchange resins and/or crystallization techniques or devices. Such processes may not reduce the odor causing bodies to a desirable level to achieve the required purity. In other words, crystallization and/or ion exchange columns may not be used to produce the MVL solutions and formulations described herein.

In one or more embodiments, the product of the above steps is a relatively colorless aqueous solution containing approximately 2 to 15 weight percent of MVL, such as mevalonic acid, based on the total weight of the solution, with impurities like color bodies and other organic species remaining in the original feed stream. Generally, in one or more embodiments, the resulting relatively colorless aqueous solution may comprise at least 0.5, 1, 1.5, or 2 and/or less than 40, 30, 25, 20, or 15 weight percent of mevalonolactone, mevalonic acid, and/or a salt of mevalonic acid, based on the total weight of the solution.

In one or more embodiments, this mevalonate solution can then be further concentrated to a desired level by evaporation or filtration techniques. For example, processing the MVL solution in a standard rotary evaporator at 50° C. and 40 mbar can remove greater than 99 percent of the water from the solution. In certain embodiments, the MVL solution is preferably concentrated to 10 weight percent, which is sufficiently high for use in various formulations.

The resulting MVL solution may be substantially free of any trace petrochemical solvents and other organic or inorganic impurities. In certain embodiments, the MVL solution is at least 95, 96, 97, 97.5, 98, 98.5, 99, or 99.5 percent pure in an aqueous solution as measured by HPLC. Absence of longer chain "polymeric" species in the resulting MVL solution may also be confirmed by gel permeation chromatography (GPC). The resulting MVL solution may be considered highly sustainable and high-purity and fit for high performance formulations for topical applications, as well as for ingestion at higher concentrations than previously possible.

Samples analyzed via HPLC may be ran on a Shimadzu HPLC equipped with a RID detector on a Bio-Rad Aminex HPX-87H column (i.e., a stainless-steel column with a 7.8 mm inside diameter and a length of 30 cm, which is packed with polystyrene divinyl benzene for liquid chromatography (5 µm in particle diameter)). HPLC samples may be ran at a constant temperature of about 50° C. and a flow rate of 0.6 mL/min, with 5 mM of sulfuric acid as the eluent. MVL may be detected at a retention time of about 17 to 18 minutes.

Alternatively, the purity analysis via HPLC may be conducted on a Beckman Coulter Gold-168 system equipped with a photodiode array detector using an Alltech reversed-phase Econosil C-18 column (10 µm, 10×250 mm) with a flow rate of 1.5 mL/min. This alternative test is described in "Bioactive sesquiterpene lactones and other compounds isolated from *Vernonia cinerea*" by Youn et al., the disclosure of which is incorporated herein by reference in its entirety.

Additionally or alternatively, the purity analysis via HPLC may be conducted using an Agilent 1200 HPLC system (Santa Clara, USA), which may be equipped with a pump, an auto sampler (ALS) (model G1329A), and a Hypersil Gold Thermo Scientific C18 (250 cm×4.6 mm) 5 µm column (Paisley, UK). The detector consists of a UV/VIS operated at 277 nm. Chemstation Software (Version Rev B.04.03 (16)) may be used for data processing and evaluation. This method is further described in "Development and Validation of an HPLC Method for Determination of Antidiabetic Drug Alogliptin Benzoate in Bulk and Tablets" by Naseef et al., the disclosure of which is incorporated herein by reference in its entirety.

In one or more embodiments, the resulting MVL solution may be substantially free of anions, cations, or trace metals. In certain embodiments, the MVL solution may comprise a cation, anion, and/or metal content of less than 10,000 ppm, 5,000 ppm, 1,000 ppm, 500 ppm, 400 ppm, 300 ppm, 200 ppm, 100 ppm, or 10 ppm, as measured by ICP-OES.

A Thermo Scientific iCAP 6000 series ICP-OES (Inductively Coupled Plasma-Optical Emission Spectrometer) may be used to carry out the trace metal analysis. This can be done by utilizing 100× dilutions of the samples, which can be prepared by diluting and mixing 100 uL of the sample with 9.9 mL of 2% nitric acid solution. Generally, calibration concentrations may range from 0 to 10 ppm for all analyzed elements.

Alternatively, ICP-OES may be conducted with a PQ 9000 Elite ICP-OES instrument, particularly for the metal analysis. Generally, calibration involved generation of linear responses between a particular element's concentration and the ICP-OES instrument may be done using a set of standards and blanks made using deionized water and reagents ($HNO_3$, HCl, $H_2O_2$) used in acid digestion. In ICP-OES, a matrix-matched solution of 1% nitric acid may be used as the calibration solution and calibration concentrations ranged from 0 to 5 ppm for all analyzed elements.

The ICP-OES analysis on the anion and cations may be performed using an iCAP 6500 ICP-OES spectrometer in radial view mode, using a quartz torch and a quartz injector tube of 2 mm inner diameter (Thermo Scientific, USA). Laser ablation (LA) is carried out with a NWR 213 nm solid state Nd:YAG laser. During LA, a gas flow of 0.9 L min−1 of helium was flushed through the cell. After the ablation chamber, a gas flow of 0.4 L min−1 Ar was added via a Y-connector. The LA-system was connected directly to the ICP-torch via 1 m of PTFE tubing of 4 mm inner diameter.

As used herein, a "high-purity" MVL refers to an MVL or MVL solution comprising a purity of at least 95 percent pure as measured by HPLC and/or a cation content of less than 10,000 ppm as measured by ICP-OES.

In various embodiments, the resulting colorless aqueous MVL solution, before or after further evaporation/concentration, may comprise at least 0.5, 1, 1.5, 2, 3, 4, 5, 10, 15, 20, 25, 30, 35, 40, 45, 50, 55, 60, 65, 70, 75, 80, 85, or 90 and/or less than 99, 90, 80, 70, 60, 50, 40, 30, 25, 20, 15, 10, 9, or 8 weight percent of mevalonolactone, mevalonic acid, and/or a salt of mevalonic acid, based on the total weight of the solution.

Due to the fermentation process described herein, the resulting MVL product can be formed almost entirely of the R-version (i.e., R-MVL). In various embodiments, the resulting colorless aqueous MVL solution, before or after further evaporation/concentration, may comprise at least 0.5, 1, 1.5, 2, 3, 4, 5, 10, 15, 20, 25, 30, 35, 40, 45, 50, 55, 60, 65, 70, 75, 80, 85, 90, 95, 99, 99.9, or 99.99 weight percent of R-MVL, based on the total weight of the solution. In certain embodiments, due to the fermentation process described herein, the MVL present in the solution or formulation may comprise at least 95, 99, 99.9, or 99.99 weight percent of R-MVL, based on the total weight of the MVL. In such embodiments, the remaining MVL can correspond to S-MVL.

In various embodiments, the resulting colorless aqueous MVL solution, before or after further evaporation/concentration, may comprise at least 0.5, 1, 1.5, 2, 3, 4, 5, 10, 15, 20, 25, 30, 35, 40, 45, 50, 55, 60, 65, 70, 75, 80, 85, or 90 and/or less than 99, 90, 80, 70, 60, 50, 40, 30, 25, 20, or 15 weight percent of water, based on the total weight of the solution.

As noted above, the resulting MVL solutions may be considered "high-purity," and, therefore, may contain little to no undesirable byproducts. In various embodiments, the resulting MVL solution, before or after further evaporation/concentration, may comprise less than 5, 4, 3, 2, 1, 0.5, 0.1, 0.05, 0.01, 0.005, 0.001, 0.0005, 0.0001, 0.00005 or 0.00001 weight percent of one or more undesirable byproducts, based on the total weight of the solution. Exemplary undesirable byproducts may include, but are not limited to, fermentation byproducts (e.g., acetic acid, citric acid, glucose, pyruvic acid, ethanol, pyruvate, glycerol, and/or lactic acid), solvents (e.g., ethyl acetate, dichloromethane, tetrahydrofuran, and/or isopropanol), petrochemicals, color bodies, odorous bodies, inorganic salts, and/or organic salts. It should be noted that the above weight ranges regarding the above undesirable byproducts may be applicable to any individual byproduct listed above or any combination thereof.

In various embodiments, the resulting MVL solution, before or after further evaporation/concentration, may comprise a petrochemical or an organic solvent content (e.g., ethyl acetate, dichloromethane, tetrahydrofuran, and/or isopropanol) of at least 0.001 parts per million and/or less than 10 parts per thousand or 10 parts per million with respect to mevalonic acid. The petrochemical origin of the impurity can be confirmed by radio isotope dating method wherein the C-14 to C-12 ratio is less than $1:1.35 \times 10^{-12}$ for the petrochemical impurity.

In various embodiments, due to the substantial absence of impurities, such as color bodies, the resulting MVL solution, before or after further evaporation/concentration, may exhibit an APHA color of less than 500, 450, 400, 350, 300, 250, 200, 150, 100, 90, 80, 70, 60, 50, 40, 30, 20, 10, 1, 0.1 or 0.01 units of parts per million of platinum-cobalt to water as measured by ASTM D1209.

Furthermore, it should be noted that fermentation products, such as mevalonic acid broths, typically have copious amounts of odor-causing bodies. Such odor-causing bodies are hard to remove and can result in end use formulations that exhibit undesirable odors. Consequently, the use of conventional fermentation products in topical skincare formulations is undesirable due to the presence of large amounts of odor-causing bodies in the fermentation products. However, contrary to previous MVL products produced by conventional methods, the inventive high-purity MVL solutions of the present disclosure have very small amounts of odor-causing bodies, which are generally removed using the inventive purification method described herein. In one or more embodiments, the resulting MVL solution, before or after further evaporation/concentration, may comprise less than 10,000 ppm, 5,000 ppm, 1,000 ppm, 500 ppm, 400 ppm, 300 ppm, 200 ppm, 100 ppm, 10 ppm or 1 ppm of odor-causing bodies as measured by gas chromatography (GC). Exemplary odor-causing bodies can include aldehydes (e.g., acetaldehyde and/or butyraldehyde), ketones (e.g., diacetyl), volatile fatty acids (e.g., propionic acid, butyric acid, valeric acid, iso-valeric acid), esters (e.g., ethyl acetate), amines (e.g., trimethylamine, indole, and/or pyridine), and/or sulfur compounds (e.g., dimethyl sulfide and/or mercaptan).

The gene modulation formulations described herein may be produced using the MVL solution before or after concentration.

This invention can be further illustrated by the following examples of embodiments thereof, although it will be understood that these examples are included merely for the purposes of illustration and are not intended to limit the scope of the invention unless otherwise specifically indicated.

EXAMPLES

Example 1—Formulation Example

A topical skin care composition (500 grams) for application to the face or body was prepared in accordance with the following process. First, 6.0 grams of Nikkomulese 41, a commercial product containing behenyl alcohol, polyglyceryl-10 pentastearate, and sodium steroyl lactylate, was combined with 2.5 grams hydrogenated lecithin, 15.0 grams squalene, 25.0 grams triethylhexanonin, 5.0 grams *Simmondsia chinensis* (Jojoba) seed oil, 5.0 grams macadamia ternifolia seed oil, 5.0 grams cyclopentasiloxane, and 0.5 grams tocopherol in a homomixer, and heated to 80° C. under continuous mixing. This mixture was labeled Fraction A. In a separate vessel, 2.0 grams phenoxyethanol was combined with 15.0 grams butylene glycol, 20.0 grams pentylene glycol, 25.0 grams of a 2 wt % xanthan gum aqueous solution, 20.0 grams of a 2 wt % NTC-Carbomer-381 aqueous solution, 15.0 grams of a 1 wt % potassium hydroxide solution, and 289 grams of de-ionized water, then heated to 80° C. under continuous mixing. This mixture was labeled Fraction B. The two fractions were combined by gradually decanting Fraction A into Fraction B, both at 80° C., under continuous mixing. The mixture was then cooled to 40° C. before addition of 2.5 grams of a 2 wt % aqueous solution of sodium hyaluronate, 2.5 grams of a 2 wt % aqueous phenoxyethanol solution, and 25.0 grams of an aqueous solution containing 10% highly sustainable high-purity mevalonolactone by weight. The resulting composition had a pH of 4.9, and a final mevalonolactone concentration of 0.5% by weight.

Example 2—Formulation Example

A sanitizing skin external composition (500 grams) for application to hands was prepared according to the following process. First, 361.95 grams of SD Alcohol 40-B (190 proof) was mixed with 5.5 grams hydroxypropylcellulose (from Ashland) and 5.0 grams of a 10 wt % aqueous solution of high-purity mevalonolactone at room temperature on a stir plate while continually stirring. Next, 121.3 grams of de-ionized water was gradually added to the mixture while stirring. Once the mixture was visually homogenous, 1.25 grams of squalene, and 5.0 grams of *Carthamus tinctorius* (Safflower) seed oil were added. The final mevalonolactone concentration of the composition was 0.1% by weight. The resulting solution had a pH of 4.5 and a viscosity of 4000 cps. All ingredients in this formula were substantially plant-based.

Consequently, this formed an innovative formulation for an alcohol-based sanitizing gel, wherein the pH was below 4.9, i.e., slightly acidic in order to support the skin's natural acidic mantle. Furthermore, such a gel formulation retained good viscosity of at least 1000 cps. Typical alcohol-based hand sanitizers (with 60 to 80% alcohol) gels are formulated with carbomer and have a pH value of neutral to slightly basic. However, this inventive formulation's slightly acidic pH property is incompatible with the typical carbomer-based formulations. In addition to pH balance, another benefit of this inventive formulation is the overall improvement in skin hydration attributable to topical application of R-MVL, which can counteract the dryness caused by alcohol-based sanitizers.

Example 3—Formulation Example

A highly sustainable, 100% plant-based, topical skin care composition for application to the face or body for gene modulation was prepared. More particularly, 1,000 grams of composition was prepared in accordance with the following methodology. First, 25 grams of a mixture of lecithin, sclerotium gum, xanthan gum, and pullulan (in a ratio of 40:35:15:10) was sprinkled into 662.8 grams of water and mixed at room temperature for 10 minutes. The mixture was labeled as Fraction A. In a separate container, 70 grams of sunflower oil was combined with 10 grams of lauroyl lysine, 10 grams of Bioxan SF T50 (Tocopherol enriched sunflower oil from Quimica Masso), and 5 grams of bakuchiol and stirred until complete homogenization. The mixture was then labeled as Fraction B. Afterwards, 50 grams of water was combined with 30 grams of 80% lactic acid in water, 50 grams of 10% mevalonolactone in water, and 50 grams of pentylene glycol under stirring until complete homogenization. This mixture was labeled as Fraction C. Subsequently, Fraction B was added to Fraction A under stirring at room temperature for 10 minutes to obtain an emulsion. Fraction C was then added to this mix under stirring for 10 minutes. Finally, approximately 37.2 grams of 20% sodium hydroxide in water solution was added to the mix under stirring until complete homogenization. The resulting composition had a pH of 4.2, and a final mevalonolactone concentration of 0.5% by weight.

The benefit of combining multiple gene expression modulating active ingredients, like MVL and bakuchiol, is the synergistic effect on the overall gene expression profile of the formulation. Such formulations can cause reduced hyperpigmentation and skin roughness and improved skin barrier in patients using the formulation.

Example 4—Assessing Effects of High-Purity MVL

Gene expression tests were conducted on EpiSkin-LM™, a commercially available 3-dimensional in-vitro human skin model composed of normal human skin cells in a collagen matrix. Test samples contained either 0.5% or 1.0% of highly sustainable, high-purity MVL by weight in a phosphate-buffered saline (PBS) solution. Negative control samples contained PBS only.

Reconstructed 3D skin epidermal models (EpiSkin-LM™) were pre-incubated with 5 mL of maintenance medium for 24 hours per manufacturer instruction. 2 mL of the test samples or negative controls were applied on the top of the epidermis. The treated models were incubated for 24 hours. After incubation, the models were rinsed with PBS, then treated again with 2 mL test samples or the negative control and incubated an additional 24 hours.

After the second incubation, mRNA was extracted from the models by miRNeasy® Mini Kit (QIAGEN). mRNA expression level in the model was measured by a Genopal® DNA microarray chip. Modulation of gene expression level was expressed as the ratio of mRNA transcripts in the test-sample treated models to mRNA transcripts in the negative control models. Positive numbers indicated an increase in gene expression, and negative numbers indicated a decrease in gene expression relative to the negative control.

Figure 2:
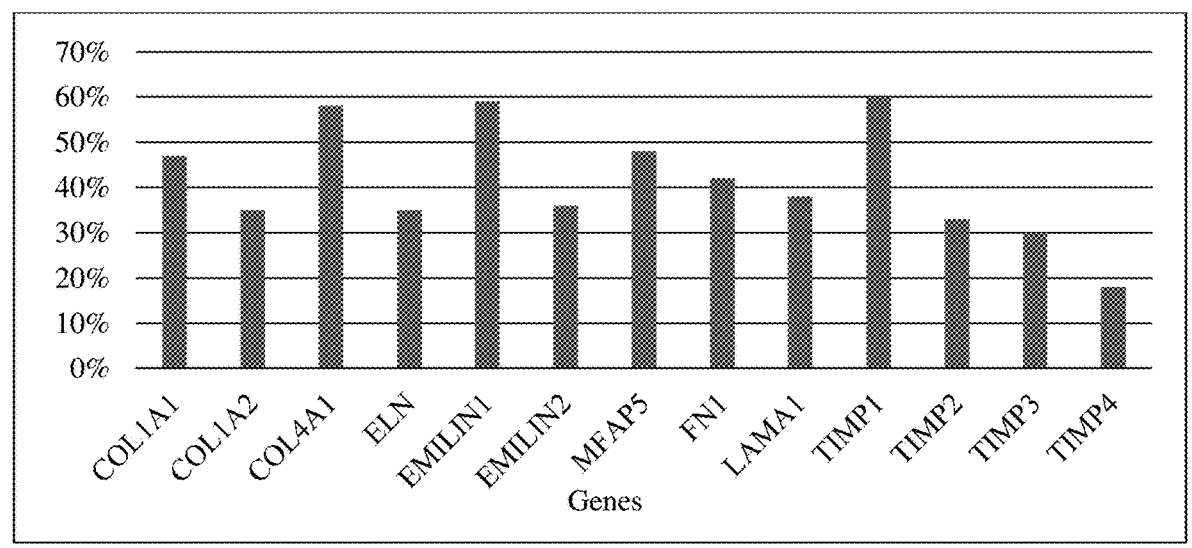
FIG. 2 is a graph showing the gene expression level (modulation) for genes related to anti-aging elasticity when models were treated with a MVL solution.

FIG. 2 shows changes in gene expression level (modulation) for genes related to anti-aging elasticity when models were treated with the solution containing 0.5% mevalolactone. In the context of the current invention, "anti-aging elasticity" refers to the maintenance and building of the extra-cellular matrix. TABLE 1, below, provides the function, as related to anti-aging elasticity, of the modulated genes depicted in FIG. 2.

TABLE 1

| Gene | Gene Function |
|---|---|
| COL1A1 | Collagen type I synthesis |
| COL1A2 | Collagen type I synthesis |
| COL4A1 | Collagen type IV synthesis |
| ELN | Elastin synthesis |
| EMILIN1 | Elastin microfibril linkage |
| EMILIN2 | Elastin microfibril linkage |
| MFAP5 | Fibrillin microfibril component |
| FN1 | Fibronectin synthesis |
| LAMA1 | Laminin synthesis |
| TIMP1 | Inhibitor of metalloproteases that degrade ECM |
| TIMP2 | Inhibitor of metalloproteases that degrade ECM |
| TIMP3 | Inhibitor of metalloproteases that degrade ECM |
| TIMP4 | Inhibitor of metalloproteases that degrade ECM |

Figure 3:
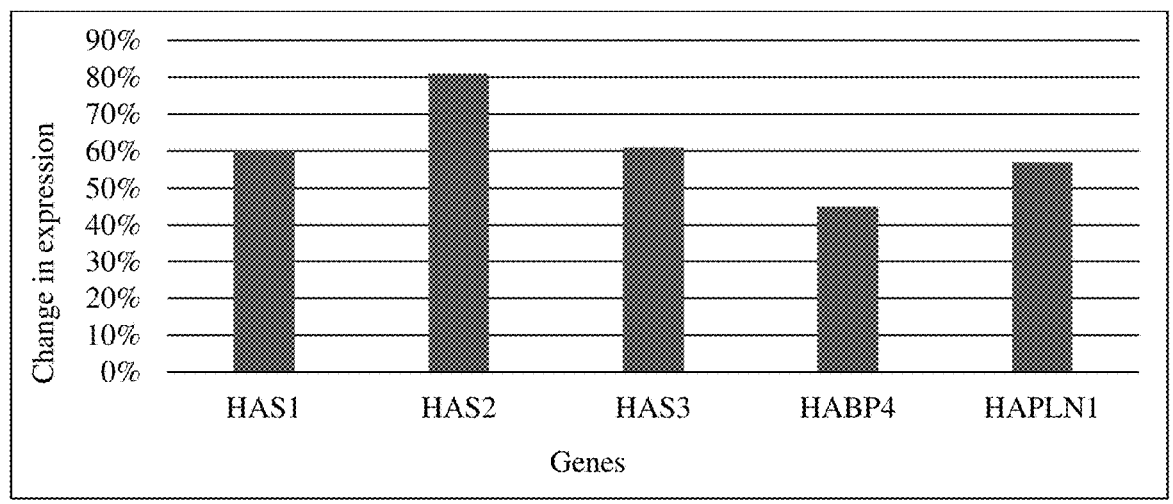
FIG. 3 is a graph showing changes in gene expression level (modulation) for genes related to moisturizing elasticity when models were treated with a MVL solution.

FIG. 3 shows changes in gene expression level (modulation) for genes related to moisturizing elasticity when models were treated with the solution containing 0.5% mevalolactone. In the context of the current invention, "moisturizing elasticity" refers to the synthesis and incorporation into the extra-cellular matrix of hyaluronic acid or hyaluronan. TABLE 2, below, shows the function, as related to moisturizing elasticity, of the modulated genes shown in FIG. 3.

TABLE 2

| Gene | Gene function |
|---|---|
| HAS1 | Hyaluronic acid synthesis |
| HAS2 | Hyaluronic acid synthesis |
| HAS3 | Hyaluronic acid synthesis |
| HABP4 | Intracellular hyaluronan binding |
| HAPLN1 | Links hyaluronan to proteoglycans in the ECM |

Figure 4:
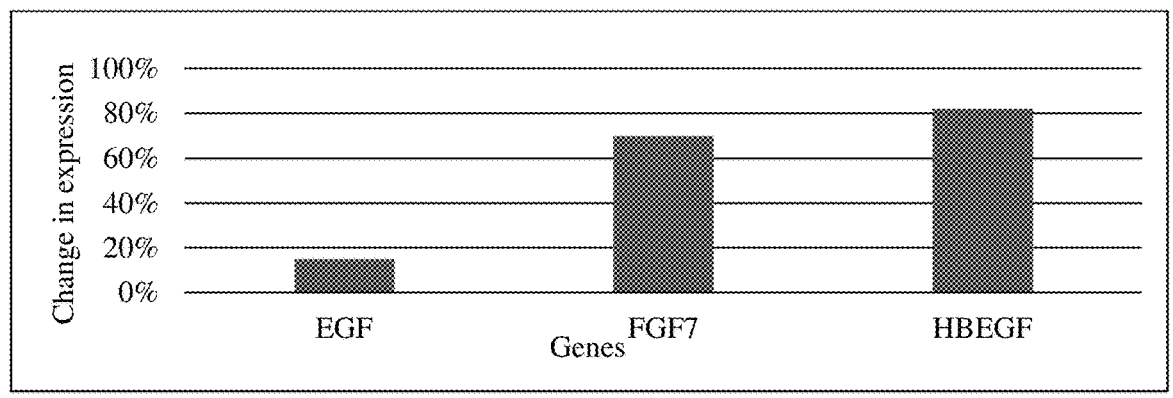
FIG. 4 is a graph showing changes in gene expression level (modulation) for genes related to epidermal turnover when models were treated with a MVL solution.

FIG. 4 shows changes in gene expression level (modulation) for genes related to epidermal turnover when models were treated with the solution containing 0.5% mevalolactone. In the context of the current invention, "epidermal turnover" refers to the process by which new keratinocyte skin cells are formed in the epidermis. TABLE 3, below, shows the function, as related to epidermal turnover, of the modulated genes shown in FIG. 4.

TABLE 3

| Gene | Gene Function |
|---|---|
| EGF | Epidermal growth factor |
| FGF7 | Keratinocyte growth Factor |
| HBEGF | Epidermal growth Factor (Heparin binding) |

Figure 5:
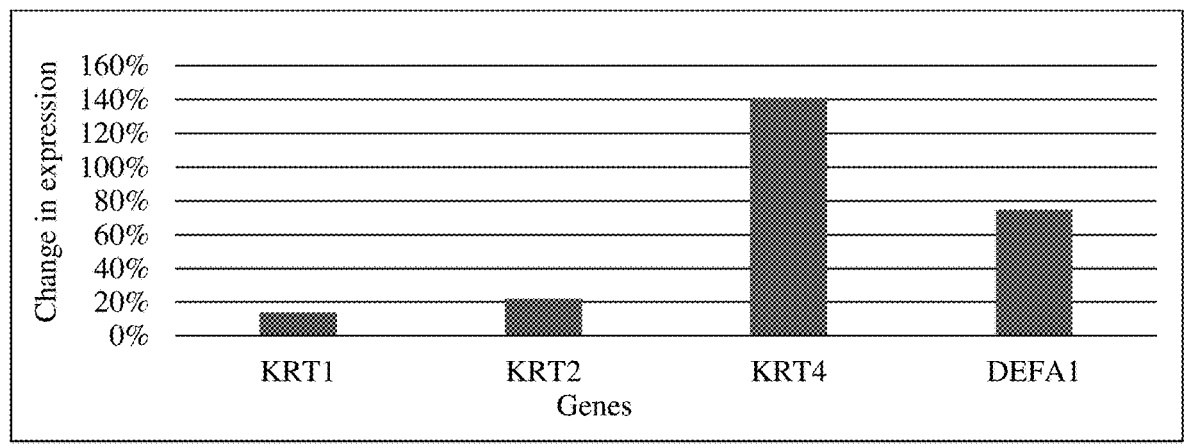
FIG. 5 is a graph showing changes in gene expression level (modulation) for genes related to barrier function when models were treated with a MVL solution.

FIG. 5 shows changes in gene expression level (modulation) for genes related to barrier function when models were treated with the solution containing 0.5% mevalolactone. In the context of the current invention, "barrier function" refers to the production and maintenance of the epithelial layer of the skin by which internal organs and tissues are separated from external environments and stimuli. Processes related to barrier function include, but are not limited to, the proliferation and differentiation of keratinocytes and the production and maintenance of keratin networks. TABLE 4, below, shows the function, as related to barrier function, of the modulated genes shown in FIG. 5.

TABLE 4

| Gene | Gene Function |
|---|---|
| KRT1 | Keratin I synthesis |
| KRT2 | Keratin II synthesis |
| KRT4 | Keratin IV synthesis |
| DEFA1 | Alpha defensin 1 synthesis |

Figure 6:
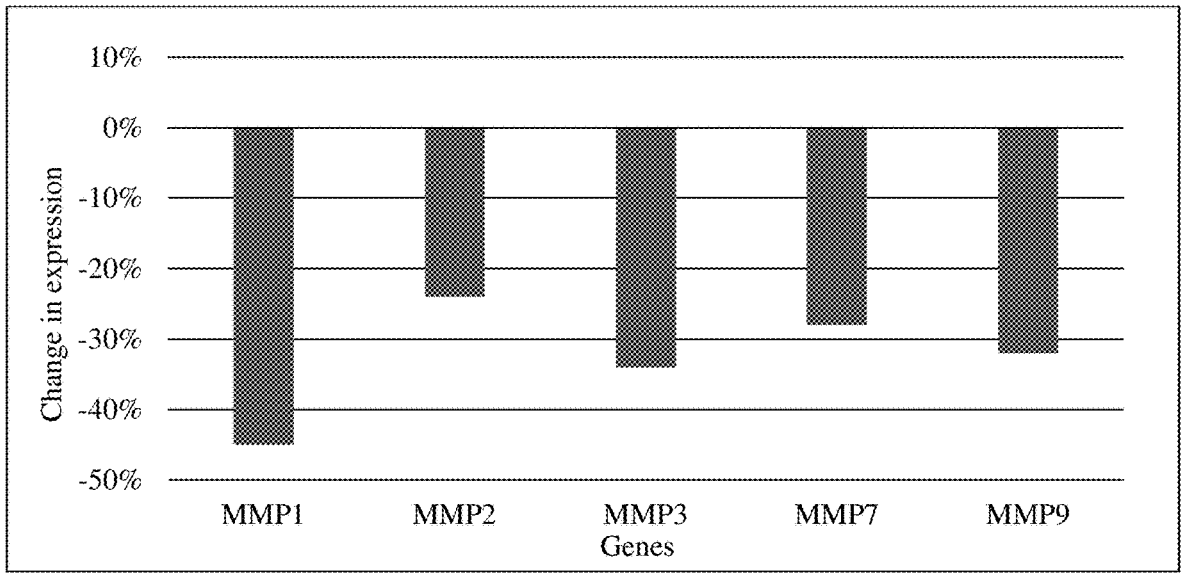
FIG. 6 is a graph showing changes in gene expression level (modulation) for genes related to extracellular matrix degradation when models were treated with a MVL solution.

FIG. 6 shows changes in gene expression level (modulation) for genes related extracellular matrix degradation when models were treated with the solution containing 1.0% mevalolactone. In the context of the current invention, "extracellular matrix degradation" refers to the break-down of major ECM components including, but not limited to, glycoproteins such as collagen, elastin, fibronectin and laminin; proteoglycans such as hyaluronic acid; hyaluronan; and other components of the ECM including casein and gelatins. TABLE 5, below, shows the function, as related to barrier function, of the modulated genes shown in FIG. 6.

TABLE 5

| Gene | Gene Function |
|---|---|
| MMP1 | Degrades collagen types I, II, and III |
| MMP2 | Degrades collagen type IV |
| MMP3 | Degrades collagen types II, III, IV, IX, and X. Degrades elastin, fibronectin, laminin. Degrades proteoglycans |
| MMP7 | Degrades fibronectin. Degrades proteoglycans. Degrades ECM components including casein, gelatins |
| MMP9 | Degrades collagen types IV and V. Degrades ECM components including gelatins |

Figure 7:
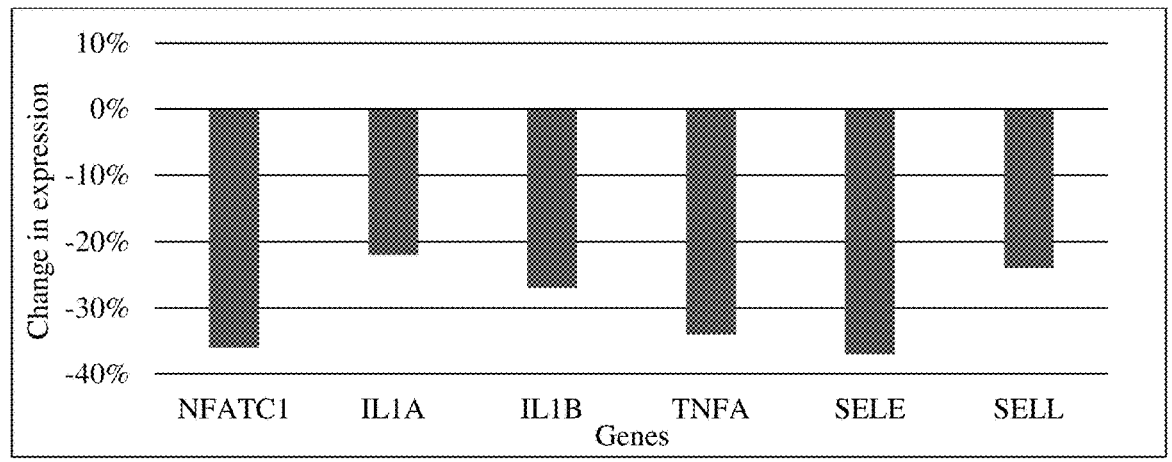
FIG. 7 is a graph showing changes in gene expression level (modulation) for genes related to skin inflammation when models were treated with a MVL solution.

FIG. 7 shows changes in gene expression level (modulation) for genes related to skin inflammation when models were treated with the solution containing 1.0% mevalolactone. In the context of the current invention, "skin inflammation" refers to the innate immune response that causes heat, pain, swelling, redness and/or loss of function on the skin. TABLE 6, below, shows the function, as related to skin inflammation, of the modulated genes shown in FIG. 7.

TABLE 6

| Gene | Gene Function |
| --- | --- |
| NFATC1 | Nuclear factor of activated T-cells. Transcription factor of immune response |
| IL1A | Proinflammatory cytokine |
| IL1B | Proinflammatory cytokine |
| TNFA | Proinflammatory cytokine |
| SELE | Selectin, promotes leukocyte aggregation during immune response |
| SELL | Selectin, promotes leukocyte aggregation during immune response |

Figure 8:
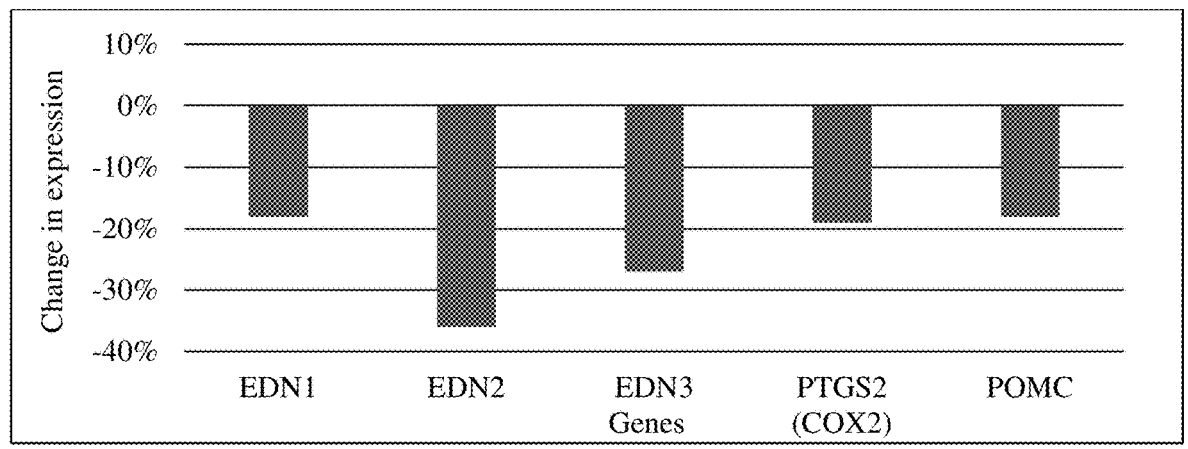
FIG. 8 is a graph showing changes in gene expression level (modulation) for genes related to skin pigmentation when models were treated with a MVL solution.

FIG. 8 shows changes in gene expression level (modulation) for genes related to skin pigmentation when models were treated with the solution containing 1.0% mevalolactone. In the context of the current invention, "skin pigmentation" refers to the production of melanin in the skin or the proliferation of melanocytes, the skin cells responsible for melanin production. TABLE 7, below, shows the function, as related to skin inflammation, of the modulated genes shown in FIG. 8.

TABLE 7

| Gene | Gene Function |
| --- | --- |
| EDN1 | Promotes melanocyte formation |
| EDN2 | Promotes melanocyte formation |
| EDN3 | Promotes melanocyte formation |
| PTGS2 (COX2) | Promotes melanin formation by melanocytes |
| POMC | Precursor of alpha melanocyte-stimulating hormone |

The data in FIGS. 2-5 shows that a composition containing 0.5% by weight of highly sustainable, high-purity R-MVL potently modulates expression of genes related to anti-aging elasticity, hydrating elasticity, epidermal turnover, and barrier function, including COL1A1, COL1A2, COL4A1, ELN, EMILIN1, EMILIN2, MFAP5, FN1, LAMA1, TIMP1, TIMP2, TIMP3, TIMP4, HAS1, HAS2, HAS3, HABP4, HAPLN1, EGF, FGF7, HBEGF, KRT1, KRT2, KRT4, and DEFA1, by increasing gene expression level by at least 10%. An increase in gene expression of at least 10% refers to a positive change in expression of magnitude 0.1 or greater relative to the negative control.

The data in FIGS. 6-8 shows that a composition containing 1.0% by weight of highly sustainable, high-purity R-MVL potently modulates expression of genes related to extracellular matrix degradation, inflammation, and skin pigmentation, including MMP1, MMP2, MMP3, MMP7, MMP9, NFATC1, IL1A, IL1B, TNFA, SELE, SELL, EDN1, EDN2, EDN3, PTGS2 (COX2), and POMC, by decreasing gene expression level by at least 10%. A decrease in gene expression of at least 10% refers to a negative change in expression of magnitude 0.1 or greater relative to the negative control.

Example 5—Assessing Gene Modulation Effects

To investigate whether the observed modulation of genes depicted in TABLES 1-7 corresponds to desirable physical and visible changes in the associated aspects of human skin, an in vivo human trial was conducted. Nine women aged 25 to 48 years (mean=34.1, std dev=8.1) participated in a four-week trial. Test samples corresponded to the composition detailed in Example 1, which contained 0.5% of highly sustainable, optically pure R-MVL by weight. The placebo preparation was the same composition without MVL. Each sample was applied to half of the face of each test subject twice per day (morning and evening) every day for four weeks. Three measurements of skin properties were made during the test; one baseline, one after two weeks, and one after four weeks. Skin hydration level was measured with a SKICON-200EX instrument. Visual skin parameters, including texture (roughness), spots, and redness, were quantified with the VISIA imaging complexion analysis system. Measurements at two and four weeks were quantified relative to the baseline measurements. Tests were conducted in the winter, when skin dryness is most common.

FIGS. 9-12 show the effects on hydration level, roughness, skin spots, and redness for skin caused by the test sample (0.5% MVL) and the placebo preparation (no MVL), expressed as a percentage of the baseline measurement.

Figure 9:
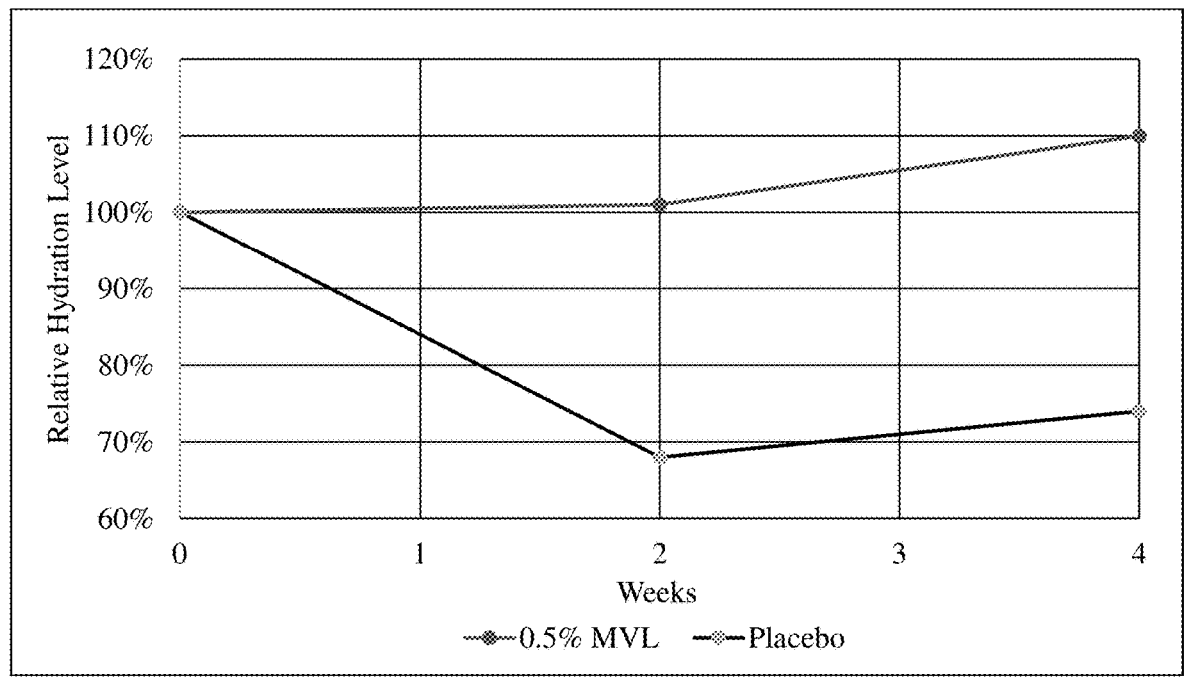
FIG. 9 is a graph comparing the effect on skin hydration level between an MVL solution and a placebo.

FIG. 9 shows the effect of the MVL composition (0.5% MVL) and the placebo composition (0% MVL) on the skin hydration level. The data in FIG. 9 shows that application of the test composition containing 0.5% by weight of highly sustainable, optically pure MVL resulted in an increased average skin hydration level compared to the placebo after both two and four weeks, with an increase of 33% at Week Two. This data highlights the hydration boosting effect of the high purity MVL in an exemplary commercial formulation containing other skin-improving agents, such as jojoba seed oil and hyaluronic acid like that presented in Example 1. After two weeks in the winter season, skin treated with the placebo (no MVL) formulation saw a slight decrease in hydration level compared to the start of the trial, whereas skin treated with the same formulation containing additionally 0.5% MVL saw a slight increase in hydration level over the baseline during the same period.

Figure 10:
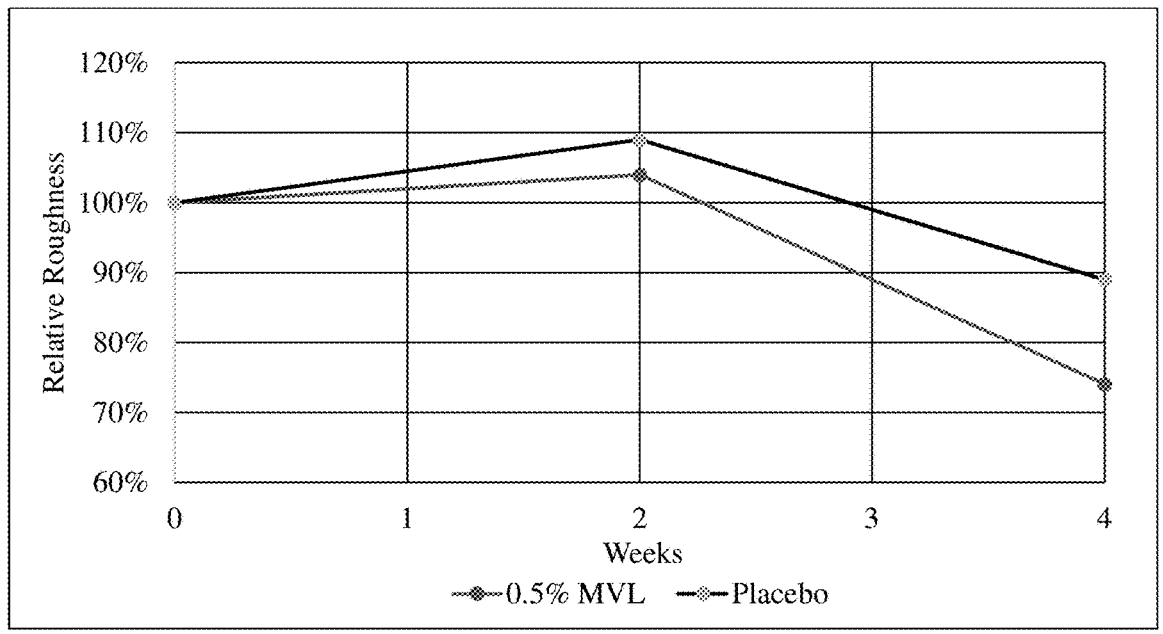
FIG. 10 is a graph comparing the effect on skin roughness between an MVL solution and a placebo.

FIG. 10 shows the effect of the MVL composition (0.5% MVL) and the placebo composition (0% MVL) on skin roughness.

Figure 11:
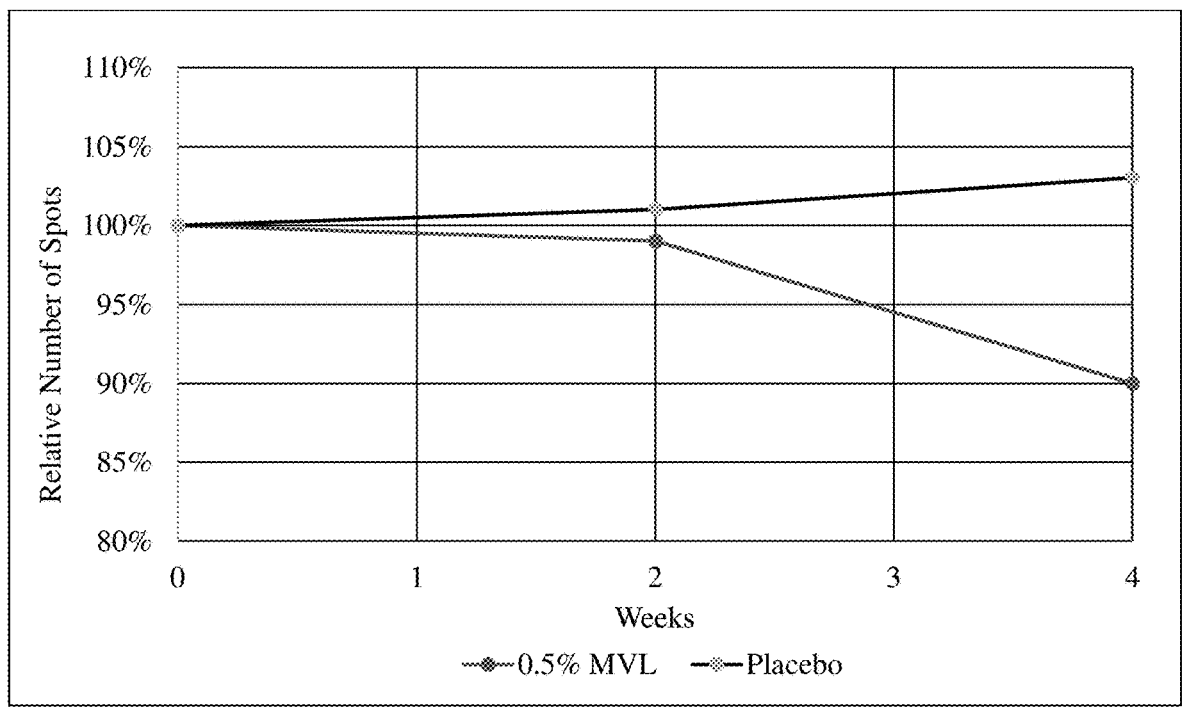
FIG. 11 is a graph comparing the effect on skin spots between an MVL solution and a placebo.

FIG. 11 shows the effect of the MVL composition (0.5% MVL) and the placebo composition (0% MVL) on skin spots.

Figure 12:
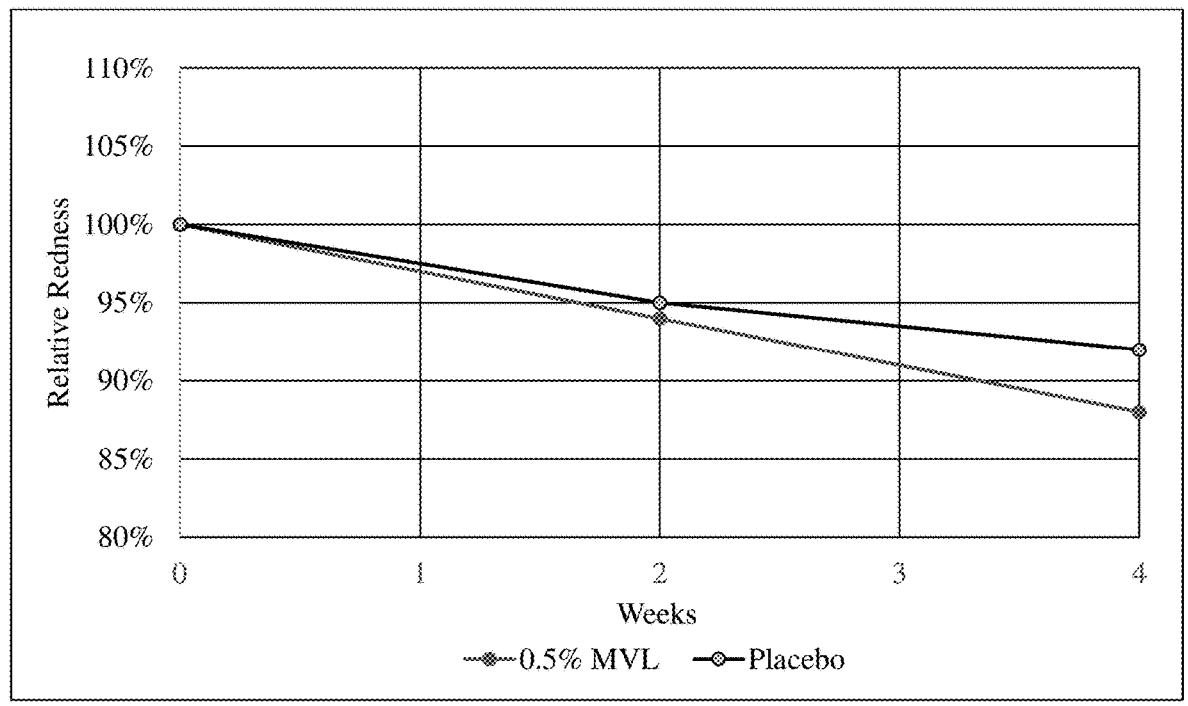
FIG. 12 is a graph comparing the effect on skin redness between an MVL solution and a placebo.

FIG. 12 shows the effect of the MVL composition (0.5% MVL) and the placebo composition (0% MVL) on skin redness.

Thus, the data in FIGS. 10-12 show that application of the test composition containing 0.5% of highly sustainable, optically pure R-MVL resulted in decreased skin roughness, spots, and redness compared to the placebo after both two and four weeks.

Example 6—Assessing MVL's Effects on Cortisol

Impact of MVL on metabolism, specifically cortisol production, was conducted on keratinocytes. Generally, 11β-HSD1 (Hydroxysteroid Dehydrogenase Type 1) converts costisone to cortisol, which then induces stress response. Impact of MVL on conversion of cortisone to cortisol was evaluated. Cortisol production tests were conducted on normal human epidermal keratinocytes cells. Test samples contained 0-0.5% of highly sustainable, high-purity MVL by weight in a phosphate-buffered saline (PBS) solution along with cortisone, an inactive form of cortisol. Negative control samples contained PBS only. Cortisol production was subsequently measured via the Alpha LISA system.

Figure 13:
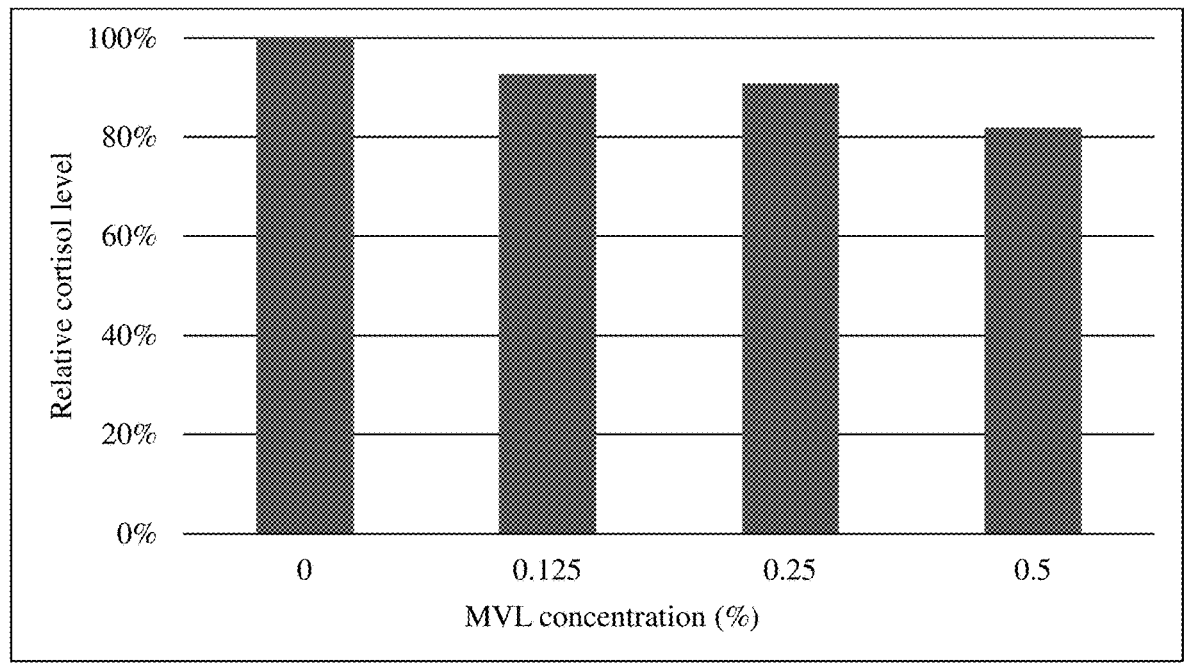
FIG. 13 is a graph showing the effects of MVL concentration on modulation of cortisol production.

The data in FIG. 13 shows that a composition containing 0.125-0.5% by weight of highly sustainable, high-purity MVL potently modulates conversion of cortisone to cortisol, with higher MVL concentrations leading to larger decline in cortisol levels. MVL at 0.5% concentration reduced cortisol production by over 15%.

Example 7—Mevalonolactone Production

An *E. coli* strain that exhibits the property of minimal flux to side products like acetic acid, citric acid, pyruvic acid, ethanol, glycerol, lactic acid, etc., by virtue of reduced activity or elimination of activity in the corresponding pathway via gene, transcript, and/or protein level changes is constructed from strain disclosed in prior art U.S. Pat. No. 10,807,963. Genes including ldhA, adhE, gltA, poxB, pta-ack are deleted using methods disclosed in prior art. This mevalonate producing strain is propagated in a 1-liter bench top bioreactor in minimal defined medium. 1 L of the minimal defined medium is be formulated with: glucose 20 g, triammonium citrate 9.2 g, potassium phosphate monobasic 1.361 g, magnesium sulfate anhydrous 0.602 g, calcium sulfate dihydrate 21.52 mg, ferrous sulfate heptahydrate 0.267 g, thiamine hydrochloride 20 mg, and trace metal solution 8 mL. 1 L of trace metal solution is formulated with: concentrated sulfuric acid 10 mL, $CoSO_4*7H_2O$ 0.6 g, $ZnSO_4*7H_2O$ 0.6 g, $Na_2MoO_4*7H_2O$ 0.2 g, $H_3BO_3$ 0.1 g, $MnSO_4*H_2O$ 0.3 g, and $CuSO_4*5H_2O$ 5 g. Final pH of medium is adjusted to 6.8 and maintained through the course of the fermentation using 5M NaOH. Temperature is maintained at 37° C. Dissolved oxygen is maintained at or above 20% of saturation level by sparging air in the range of 0.5-1 liters per minute (LPM) and agitation in the range of 600-1100 rpm. 15 hours after mevalonate production is induced. Anti-foam is added as needed. Glucose concentration is maintained between 1-3 g/l by addition of 600 g/l glucose at 1-hour intervals. The bioreactor run is stopped at 96 hours. Cells were separated from the broth by use of 0.22 micron filters to obtain clear broth. Mevalonate concentration was found to be 79 g/l at the end of fermentation as depicted in FIG. 1.

Figure 14:
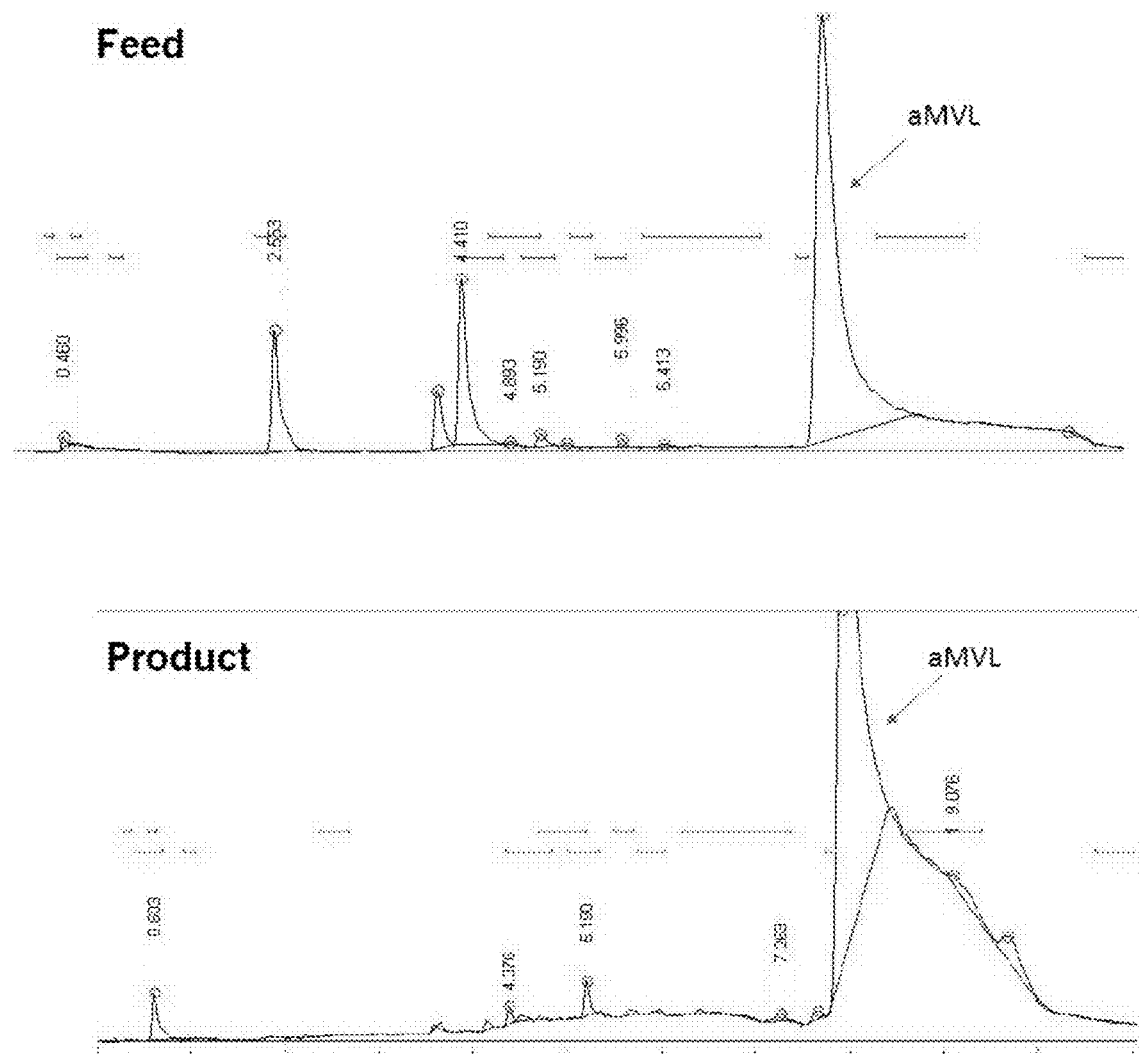
FIG. 14 depicts two GC-FID chromatograms comparing the presence of impurities before and after electrodialysis process.

This clarified broth was circulated in an electrodialysis device similar to the Acilyzer system from Astom Corporation, to selectively isolate charged products like mevalonate salt. The system was run at 5V/cell pair in a recirculation mode for 5 hours. The feed was 79 g/l mevalonate at the start. The product stream obtained at the end of first cycle was 40 g/l pure mevalonate which was higher in purity, with lower odor and color relative to the feed as characterized by GC-FID depicted in FIG. 14.

Example 8—Assessing MVL's Effects on Hyaluronic Acid

Impact of MVL on hyaluronic acid, was conducted on keratinocytes. Hyaluronic acid is a crucial component of the skin. Impact of MVL on conversion of hyaluronic acid was evaluated. Hyaluronic acid tests were conducted on normal human epidermal keratinocytes (NHEKs) cells. Test samples contained 0-0.25% of highly sustainable, high-purity MVL by weight in a phosphate-buffered saline (PBS) solution. Negative control samples contained PBS only. Hyaluronic acid level in the medium was subsequently measured at 24 hours and 48 hours via ELISA and normalized to the protein level in the NHEK cells.

Figure 15:
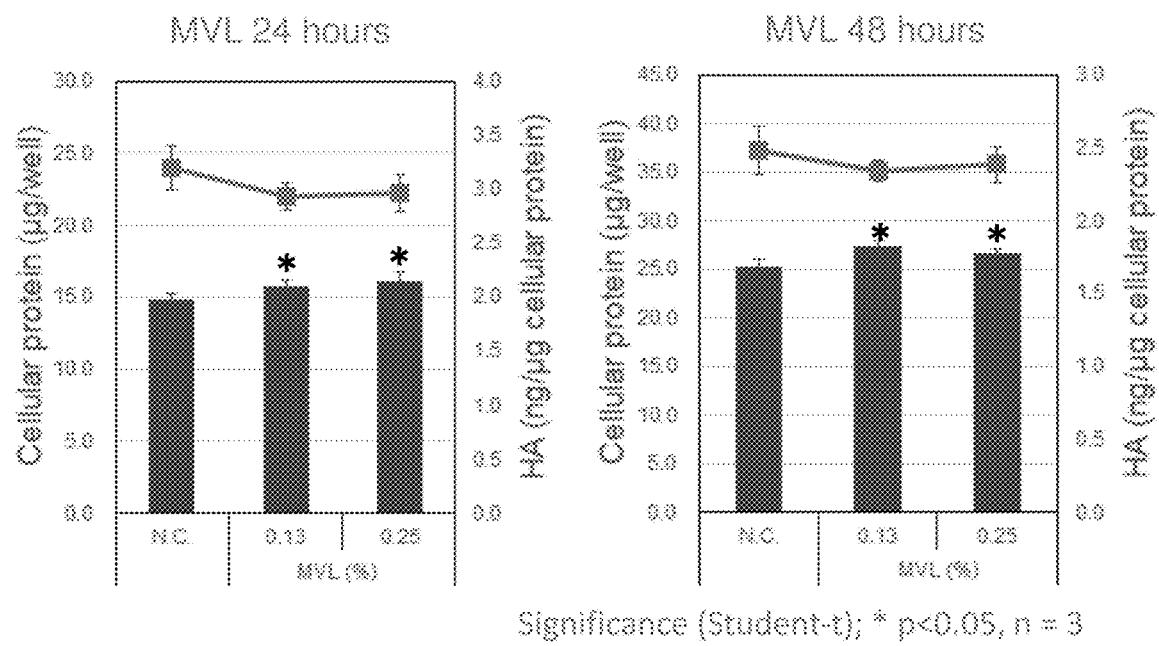
FIG. 15 is a graph showing the effects of MVL concentration on modulation of hyaluronic acid levels.

The data in FIG. 15 shows that a composition containing 0.13-0.25% by weight of highly sustainable, high-purity MVL potently modulates hyaluronic acid levels, with higher MVL concentrations leading to higher hyaluronic acid levels. MVL at 0.13% and 0.25% concentration both increased hyaluronic acid levels by over 5% in 48 hours (p-value: $p<0.05$).

Definitions

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "about" refers to values within 10 percent of the stated value. For example, "about 10" would correspond to values in the range of 9 to 11.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "include," and "included" have the same open-ended meaning as "comprising," "comprises," and "comprise" provided above.

NUMERICAL RANGES

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

Furthermore, terms leading a recited range containing a plurality of numerical values, such as "at least," "not more than," and "less than," apply to all of the numerical values recited in the range listing. For example, "at least 1, 2, 3, or 4" should be interpreted as covering ranges of "at least 1, at least 2, at least 3, or at least 4."

CLAIMS NOT LIMITED TO DISCLOSED EMBODIMENTS

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

What is claimed is:

1. A gene modulation formulation comprising mevalonolactone for modulating expression of one or more genes selected from group consisting of: COL1A1, COL1A2, COL4A1, ELN, EMILIN1, EMILIN2, MFAP5, FN1, LAMA1, TIMP1, TIMP2, TIMP3, TIMP4, HAS1, HAS2, HAS3, HABP4, HAPLN1, EGF, FGF7, HBEGF, KRT1, KRT2, KRT4, DEFA1, MMP1, MMP2, MMP3, MMP7, MMP9, NFATC1, IL1A, IL1B, TNFA, SELE, SELL, EDN1, EDN2, EDN3, PTGS2 (COX2), and POMC by at least 10 percent within 24 hours in epithelial tissue; wherein said mevalonolactone:
   (a) is at least 97.5 percent pure in an aqueous solution as measured by HPLC,
   (b) comprises less than 1 weight percent of fermentation byproducts, ethyl acetate, dichloromethane, tetrahydrofuran, isopropanol, petrochemicals, or combinations thereof, based on the total weight of said mevalonolactone, and
   (c) comprises less than 10,000 ppm of odor-causing bodies as measured by gas chromatography (GC),
   wherein said gene modulation formulation comprises 0.05 to 10 weight percent of said mevalonolactone.

2. The gene modulation formulation of claim 1, wherein said mevalonolactone is at least 98.5 or 99.5 percent pure in an aqueous solution as measured by HPLC.

3. The gene modulation formulation of claim 1, wherein said mevalonolactone is in the form of an aqueous solution comprising said mevalonolactone.

4. The gene modulation formulation of claim 1, wherein said gene modulation formulation increases expression of at least two genes selected from group consisting of: COL1A1, COL1A2, COL4A1, ELN, EMILIN1, EMILIN2, MFAP5, FN1, LAMA1, TIMP1, TIMP2, TIMP3, TIMP4, HAS1, HAS2, HAS3, HABP4, HAPLN1, EGF, FGF7, HBEGF, KRT1, KRT2, KRT4, and DEFA1 by at least 10 percent as measured 24 hours after application.

5. The gene modulation formulation of claim 1, wherein said gene modulation formulation decreases expression of at least two genes selected from group consisting of: MMP1, MMP2, MMP3, MMP7, MMP9, NFATC1, IL1A, IL1B, TNFA, SELE, SELL, EDN1, EDN2, EDN3, PTGS2 (COX2), and POMC by at least 10 percent as measured 24 hours after application.

6. The gene modulation formulation of claim 1, wherein said gene modulation formulation decreases production of cortisol in human epithelial skin cells by at least 10 percent as measured 24 hours after application.

7. The gene modulation formulation of claim 1, wherein said mevalonolactone comprises at least 95 weight percent of R-mevalonolactone based on the total weight of said mevalonolactone.

8. The gene modulation formulation of claim 1, wherein said gene modulation formulation is a topical skincare composition in the form of a mist, a lotion, an emulsion, a gel, a cream, or an ointment.

9. The gene modulation formulation of claim 1, wherein said mevalonolactone comprises less than 1, 0.5, 0.1, 0.05, 0.01, 0.005, 0.001, 0.0005, 0.0001, 0.00005 or 0.00001 weight percent of fermentation byproducts, ethyl acetate, dichloromethane, tetrahydrofuran, isopropanol, petrochemicals, or combinations thereof, based on the total weight of said mevalonolactone.

10. The gene modulation formulation of claim 1, wherein said mevalonolactone comprises a cation, anion, and/or metal content of less than 10,000 ppm, 5,000 ppm, 1,000 ppm, 500 ppm, 400 ppm, 300 ppm, 200 ppm, 100 ppm, or 10 ppm, as measured by ICP-OES.

11. The gene modulation formulation of claim 1, wherein said formulation comprises at least 0.5, 1, 1.5, 2, 3, 4, 5, 10, 15, 20, 25, 30, 35, 40, 45, 50, 55, 60, 65, 70, 75, 80, 85, or 90 and/or less than 99, 90, 80, 70, 60, 50, 40, 30, 25, 20, 15, 10, 9, or 8 weight percent of mevalonolactone, mevalonic acid, and/or a salt of mevalonic acid, based on the total weight of the formulation.

12. The gene modulation formulation of claim 1, wherein said mevalonolactone exhibits an APHA color of less than 500, 450, 400, 350, 300, 250, 200, 150, 100, 90, 80, 70, 60, 50, 40, 30, 20, 10, 1, 0.1 or 0.01 units of parts per million of platinum-cobalt to water as measured by ASTM D1209.

13. The gene modulation formulation of claim 1, wherein said formulation comprises less than 5,000 ppm, 1,000 ppm, 500 ppm, 400 ppm, 300 ppm, 200 ppm, 100 ppm, or 10 ppm of odor-causing bodies as measured by gas chromatography (GC).

14. The gene modulation formulation of claim 1, wherein said mevalonolactone is purified in a wiped film evaporator, a rotary evaporator, and/or a falling film evaporator.

15. A method of forming a dermatological formulation, said method comprising:
   (a) providing an aqueous solution of mevalonolactone, wherein said mevalonolactone is—
      (i) is at least 97.5 percent pure in an aqueous solution as measured by HPLC,
      (ii) comprises less than 1 weight percent of fermentation byproducts, ethyl acetate, dichloromethane, tetrahydrofuran, isopropanol, petrochemicals, or combinations thereof, based on the total weight of said mevalonolactone, and
      (iii) comprises less than 10,000 ppm of odor-causing bodies as measured by gas chromatography (GC); and
   (b) combining said aqueous solution with at least one additive to thereby form said dermatological formulation,
   wherein said formulation comprises 0.05 to 10 weight percent of said mevalonolactone and modulates expression of one or more genes selected from group consisting of COL1A1, COL1A2, COL4A1, ELN, EMILIN1, EMILIN2, MFAP5, FN1, LAMA1, TIMP1, TIMP2, TIMP3, TIMP4, HAS1, HAS2, HAS3, HABP4, HAPLN1, EGF, FGF7, HBEGF, KRT1, KRT2, KRT4, DEFA1, MMP1, MMP2, MMP3, MMP7, MMP9, NFATC1, IL1A, IL1B, TNFA, SELE, SELL, EDN1, EDN2, EDN3, PTGS2 (COX2), and POMC by at least 10 percent within 24 hours in epithelial tissue.

16. The method of claim 15, wherein said mevalonolactone is at least 98.5 or 99.5 percent pure in an aqueous solution as measured by HPLC.

17. The method of claim 15, wherein said mevalonolactone is in the form of an aqueous solution comprising said mevalonolactone.

18. The method of claim 15, wherein said dermatological formulation increases expression of at least two genes selected from group consisting of: COL1A1, COL1A2, COL4A1, ELN, EMILIN1, EMILIN2, MFAP5, FN1, LAMA1, TIMP1, TIMP2, TIMP3, TIMP4, HAS1, HAS2, HAS3, HABP4, HAPLN1, EGF, FGF7, HBEGF, KRT1, KRT2, KRT4, and DEFA1 by at least 10 percent as measured 24 hours after application.

19. The method of claim 15, wherein said dermatological formulation decreases expression of at least two genes selected from group consisting of: MMP1, MMP2, MMP3, MMP7, MMP9, NFATC1, IL1A, IL1B, TNFA, SELE, SELL, EDN1, EDN2, EDN3, PTGS2 (COX2), and POMC by at least 10 percent as measured 24 hours after application.

20. The method of claim 15, wherein said dermatological formulation decreases production of cortisol in human epithelial skin cells by at least 10 percent as measured 24 hours after application.

21. The method of claim 15, wherein said mevalonolactone comprises at least 95 weight percent of R-mevalonolactone based on the total weight of said mevalonolactone.

22. The method of claim 15, wherein said dermatological formulation is a topical skincare composition in the form of a mist, a lotion, an emulsion, a gel, a cream, or an ointment.

23. The method of claim 15, wherein said mevalonolactone comprises less than 1, 0.5, 0.1, 0.05, 0.01, 0.005, 0.001, 0.0005, 0.0001, 0.00005 or 0.00001 weight percent of fermentation byproducts, ethyl acetate, dichloromethane, tetrahydrofuran, isopropanol, petrochemicals, or combinations thereof, based on the total weight of said mevalonolactone.

24. The method of claim 15, wherein said mevalonolactone comprises a cation, anion, and/or metal content of less than 10,000 ppm, 5,000 ppm, 1,000 ppm, 500 ppm, 400 ppm, 300 ppm, 200 ppm, 100 ppm, or 10 ppm, as measured by ICP-OES.

25. The method of claim 15, wherein said mevalonolactone exhibits an APHA color of less than 500, 450, 400, 350, 300, 250, 200, 150, 100, 90, 80, 70, 60, 50, 40, 30, 20, 10, 1, 0.1 or 0.01 units of parts per million of platinum-cobalt to water as measured by ASTM D1209.

26. The method of claim 15, wherein said dermatological formulation comprises at least 0.5, 1, 1.5, 2, 3, 4, 5, 10, 15, 20, 25, 30, 35, 40, 45, 50, 55, 60, 65, 70, 75, 80, 85, or 90 and/or less than 99, 90, 80, 70, 60, 50, 40, 30, 25, 20, 15, 10, 9, or 8 weight percent of mevalonolactone, mevalonic acid, and/or a salt of mevalonic acid, based on the total weight of the formulation.

27. The method of claim 15, wherein said dermatological formulation comprises less than 5,000 ppm, 1,000 ppm, 500 ppm, 400 ppm, 300 ppm, 200 ppm, 100 ppm, or 10 ppm of odor-causing bodies as measured by gas chromatography (GC).

28. The method of claim 15, wherein said mevalonolactone is purified in a wiped film evaporator, a rotary evaporator, and/or a falling film evaporator.

29. The method of claim 15, wherein said providing comprises:
fermenting an initial feedstock to thereby form an unpurified solution comprising mevalonolactone, mevalonic acid, and/or a salt of mevalonic acid;
contacting said unpurified solution with an acid to thereby form an acidic mixture; and
purifying said acidic mixture with a wiped film evaporator, a falling film evaporator, a rotary evaporator, an electrodialysis device, and/or an electro-deionization device to thereby form a purified solution comprising mevalonolactone, mevalonic acid, and/or a salt of mevalonic acid.

30. The method of claim 15, wherein said providing comprises:
fermenting an initial feedstock to thereby form an unpurified solution comprising mevalonolactone, mevalonic acid, and/or a salt of mevalonic acid;
contacting said unpurified solution with an acid to thereby form an acidic mixture;
purifying said acidic mixture with a falling film evaporator and/or a rotary evaporator to form a purified solution; and
optionally further purifying said purified solution in a wiped film evaporator.

31. The method of claim 15, wherein said providing comprises:
fermenting an initial feedstock to thereby form an unpurified solution comprising mevalonolactone, mevalonic acid, and/or a salt of mevalonic acid;
contacting said unpurified solution with an acid to thereby form an acidic mixture;
purifying said acidic mixture in a electrodialysis device and/or an electro-deionization device.

32. A purified mevalonolactone solution comprising:
(a) mevalonolactone, wherein said mevalonolactone:
(i) is at least 97.5 percent pure in an aqueous solution as measured by HPLC,
(ii) comprises less than 1 weight percent of fermentation byproducts, ethyl acetate, dichloromethane, tetrahydrofuran, isopropanol, petrochemicals, or combinations thereof, based on the total weight of said mevalonolactone, and
(iii) comprises less than 10,000 ppm of odor-causing bodies as measured by gas chromatography (GC); and
(b) water,
wherein said solution modulates expression of one or more genes selected from group consisting of COL1A1, COL1A2, COL4A1, ELN, EMILIN1, EMILIN2, MFAP5, FN1, LAMA1, TIMP1, TIMP2, TIMP3, TIMP4, HAS1, HAS2, HAS3, HABP4, HAPLN1, EGF, FGF7, HBEGF, KRT1, KRT2, KRT4, DEFA1, MMP1, MMP2, MMP3, MMP7, MMP9, NFATC1, IL1A, IL1B, TNFA, SELE, SELL, EDN1, EDN2, EDN3, PTGS2 (COX2) and POMC by at least 10 percent within 24 hours in epithelial tissue.

33. The purified mevalonolactone method of claim 32, wherein said mevalonolactone is at least 99 or 99.5 percent pure in an aqueous solution as measured by HPLC.

34. The purified mevalonolactone method of claim 32, wherein said solution increases expression of at least two genes selected from group consisting of: COL1A1, COL1A2, COL4A1, ELN, EMILIN1, EMILIN2, MFAP5, FN1, LAMA1, TIMP1, TIMP2, TIMP3, TIMP4, HAS1, HAS2, HAS3, HABP4, HAPLN1, EGF, FGF7, HBEGF, KRT1, KRT2, KRT4, and DEFA1 by at least 10 percent as measured 24 hours after application.

35. The purified mevalonolactone method of claim 32, wherein said solution decreases expression of at least two genes selected from group consisting of: MMP1, MMP2, MMP3, MMP7, MMP9, NFATC1, IL1A, IL1B, TNFA, SELE, SELL, EDN1, EDN2, EDN3, PTGS2 (COX2), and POMC by at least 10 percent as measured 24 hours after application.

36. The purified mevalonolactone method of claim 32, wherein said solution decreases production of cortisol in human epithelial skin cells by at least 10 percent as measured 24 hours after application.

37. The purified mevalonolactone method of claim 32, wherein said mevalonolactone comprises at least 95 weight percent of R-mevalonolactone based on the total weight of said mevalonolactone.

38. The purified mevalonolactone method of claim 32, wherein said mevalonolactone comprises less than 1, 0.5, 0.1, 0.05, 0.01, 0.005, 0.001, 0.0005, 0.0001, 0.00005 or 0.00001 weight percent of fermentation byproducts, ethyl acetate, dichloromethane, tetrahydrofuran, isopropanol, petrochemicals, or combinations thereof, based on the total weight of said mevalonolactone.

39. The purified mevalonolactone method of claim 32, wherein said mevalonolactone comprises a cation, anion, and/or metal content of less than 10,000 ppm, 5,000 ppm, 1,000 ppm, 500 ppm, 400 ppm, 300 ppm, 200 ppm, 100 ppm, or 10 ppm, as measured by ICP-OES.

40. The purified mevalonolactone method of claim 32, wherein said solution comprises at least 0.5, 1, 1.5, 2, 3, 4, 5, 10, 15, 20, 25, 30, 35, 40, 45, 50, 55, 60, 65, 70, 75, 80, 85, or 90 and/or less than 99, 90, 80, 70, 60, 50, 40, 30, 25, 20, 15, 10, 9, or 8 weight percent of mevalonolactone, mevalonic acid, and/or a salt of mevalonic acid, based on the total weight of the formulation.

41. The purified mevalonolactone method of claim 32, wherein said mevalonolactone exhibits an APHA color of less than 500, 450, 400, 350, 300, 250, 200, 150, 100, 90, 80, 70, 60, 50, 40, 30, 20, 10, 1, 0.1 or 0.01 units of parts per million of platinum-cobalt to water as measured by ASTM D1209.

42. The purified mevalonolactone method of claim 32, wherein said formulation comprises less than 5,000 ppm, 1,000 ppm, 500 ppm, 400 ppm, 300 ppm, 200 ppm, 100 ppm, or 10 ppm of odor-causing bodies as measured by gas chromatography (GC).

43. The purified mevalonolactone method of claim 32, wherein said mevalonolactone is purified in a wiped film evaporator, a rotary evaporator, and/or a falling film evaporator.

* * * * *